United States Patent [19]

Chu et al.

[11] Patent Number: 5,624,924

[45] Date of Patent: Apr. 29, 1997

[54] QUINOBENZOTHIAZINE ANTINEOPLASTIC AGENTS

[75] Inventors: Daniel T. Chu, Vernon Hills; Jacob J. Plattner, Libertyville, both of Ill.; Robert Hallas, Kenosha, Wis.

[73] Assignee: Abbott Laboratories, Abbott Park, Ill.

[21] Appl. No.: 254,801

[22] Filed: Jun. 6, 1994

Related U.S. Application Data

[60] Division of Ser. No. 842,910, Feb. 27, 1992, Pat. No. 5,318,965, which is a continuation-in-part of Ser. No. PCT/US91/06040, Aug. 23, 1991, which is a continuation-in-part of Ser. No. 573,102, Aug. 24, 1990, abandoned.

[51] Int. Cl.$^6$ .................. C07D 279/36; A61K 31/54
[52] U.S. Cl. ............................. 514/224.5; 544/14
[58] Field of Search ................. 544/514; 514/224.5

[56] References Cited

U.S. PATENT DOCUMENTS

| | | | |
|---|---|---|---|
| 4,529,725 | 7/1985 | Chu | 514/223 |
| 4,533,663 | 8/1985 | Chu | 514/223 |

OTHER PUBLICATIONS

Chu, Chemical Abstracts, vol. 104, entry 148892 (1985).
Chu, Chemical Abstracts, vol. 104, entry 198598 (1985).
Chu, Chemical Abstracts, vol. 104, entry 5885 (1985).

*Primary Examiner*—John M. Ford
*Attorney, Agent, or Firm*—Mona Anand

[57] ABSTRACT

Quinobenzothiazine derivatives of the formula

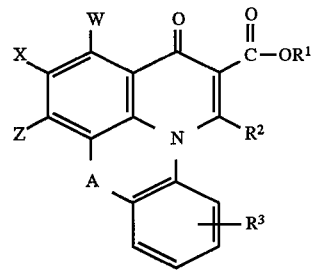

as well as the pharmaceutically acceptable salts, esters, amides and prodrugs thereof are disclosed, wherein $R^1$ is hydrogen or acarboxy-protecting group, $R^2$ and $R^3$ are substitutents, A is oxygen, sulfur, or carbon, Z is a halogen or a nitrogen-containing group, X is hydrogen, halogen or alkyl, and W is hydrogen, alkyl, amino or halogen. The compounds have potent antineoplastic activity.

10 Claims, No Drawings

QUINOBENZOTHIAZINE ANTINEOPLASTIC AGENTS

This is a division of U.S. patent application Ser. No. 07/842,910, filed Feb. 27, 1992, now U.S. Pat. No. 5,318, 965, which is a continuation-in-part of the international patent application Ser. No. PCT/US91/06040 (in which the United States is a designated country), filed Aug. 23, 1991, the specification of which is incorporated herein by reference, which is a continuation-in-part of U.S. patent application Ser. No. 07/573,102, filed Aug. 24, 1990, and now abandoned.

TECHNICAL FIELD

This invention relates to compounds which have antineoplastic activity. More particularly, this invention concerns quinobenzoxazine, quinobenzothiazine, and pyrido-acridine derivatives that are useful in the treatment of neoplastic diseases, pharmaceutical compositions containing these compounds, and to methods of treating neoplastic diseases with such quinobenzoxazine, quinobenzothiazine, and pyrido-acridine derivatives.

BACKGROUND OF THE INVENTION

It is known that certain quinolone compounds possess antibacterial activities. For example, D. Chu, U.S. Pat. No. 4,607,032, issued Aug. 19, 1986, which is incorporated herein by reference, has disclosed 1-substituted amino-2-fluoro-4-oxo-4H-quino[2,3,4-i,j][1,4]benzoxazine-5-carboxylic acid derivatives which possess antibacterial activity. Closely related quinobenzothiazine and quinobenzoxazine derivatives having antibacterial activity have also been disclosed by Chu in U.S. Pat. No. 4,528,285, issued Jul. 9, 1985; U.S. Pat. No. 4,529,725, issued Jul. 16, 1985; and U.S. Pat. No. 4,542,133, issued Sep. 17, 1985. However, these and other related novel derivatives have not been known heretofore to be antineoplastic agents.

SUMMARY OF THE INVENTION

In one aspect of the present invention there is provided a method of treating neoplastic diseases comprises administering to a host animal in need of such treatment a therapeutically effective amount of a compound of the Formula I:

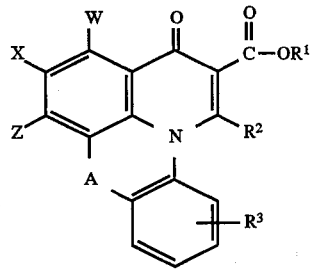

or a pharmaceutically acceptable salt, ester, amide or prodrug therof, in which $R^1$ is selected from hydrogen and a carboxy-protecting group. Such compounds are now unexpectedly found to possess a high degree of antineoplastic activity, as measured both in vitro and in vivo.

$R^2$ in Formula I is selected from hydrogen, alkyl of from 1 to 6 carbon atoms, alkoxy of from 1 to 6 carbon atoms, and sulfhydroalkyl of from 1 to 6 carbon atoms.

$R^3$ in Formula I is one or more groups independently selected from the group consisting of hydrogen; halogen; nitro; alkyl of from 1 to 6 carbon atoms; carboxyl; methylenedioxy; cyano; halo-substituted alkyl of from 1 to 6 carbon atoms; hydroxy-substituted alkyl of from 1 to 6 carbon atoms; alkylsulfonyl; methylenedioxy; a group of the formula —$YR^4$ wherein Y is O or S, and $R^4$ is hydrogen or alkyl of from 1 to 6 carbon atoms; and an amine of the formula —$NR^5R^6$ wherein $R^5$ and $R^6$ are independently selected from hydrogen or alkyl of from 1 to 6 carbon atoms.

W in Formula I is selected from hydrogen, alkoxy, hydroxyl, alkyl of from 1 to 6 carbon atoms, amino, alkylamino, and halogen, and halo-substituted alkyl.

X in Formula I is selected from halogen, hydrogen, alkyl of from 1 to 6 carbon atoms, and halo-substituted alkyl of from 1 to 6 carbon atoms.

Z in Formula I is selected from (a) halogen; (b) a pyridyl or substituted pyridyl group; (c) an amino group of the formula —$NR^{12}R^{13}$ wherein $R^{12}$ is hydrogen or alkyl of from 1 to 10 carbon atoms and $R^{13}$ is selected from alkyl of from 1 to 10 carbon atoms, hydroxy-substituted alkyl of from 1 to 10 carbon atoms, an amino group, an alkylamino of from 1 to 6 carbon atoms, and dialkylamino of from 1 to 6 carbon atoms; and (d) a nitrogen-containing heterocycle of the formula

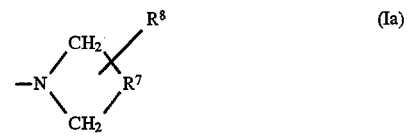

wherein $R^7$ is selected from —$CH_2$—, —$CH_2CH_2$—, —$CH_2CH_2CH_2$—, —$CH_2CH_2NHCH_2$—, or a group of the formula —$CH_2R^9CH_2$— wherein $R^9$ is selected from S, O, or NH. $R^8$ in Formula Ia is 1 or 2 groups independently selected from hydrogen, alkyl of from 1 to 6 carbon atoms, halo-substituted alkyl of from 1 to 6 carbon atoms, amino-substituted alkyl of from 1 to 6 carbon atoms, hydroxy-substituted alkyl of from 1 to 6 carbon atoms, alkylaminoalkyl of from 1 to 6 carbon atoms, hydroxy, alkanoyl of from 1 to 6 carbon atoms, a spirocycloalkyl group and an amine of the formula —$NR^{10}R^{11}$. $R^{10}$ and $R^{11}$ in this instance may be independently selected from hydrogen and alkyl of from 1 to 6 carbon atoms, or, alternatively, one of $R^{10}$ and $R^{11}$ is hydrogen and the other is an alkanoyl group or a peptidyl group of from 1 to 5 α-amino acids joined to the nitrogen with an amide linkage.

Alternatively, X and Z may be taken together to form —$OCH_2O$— or —$OCH_2CH_2$—.

A in Formula I is selected from O, S and $CH_2$.

In another aspect of the present invention, there are provided novel compounds and pharmaceutical compositions thereof having Formula I wherein $R^1, R^2, R^3, A, W$, and X are described as above. In these compounds, Z is selected from (a) pyridyl or substituted pyridyl, with the proviso that A is not S, and (b) a nitrogen-containing heterocycle of the formula

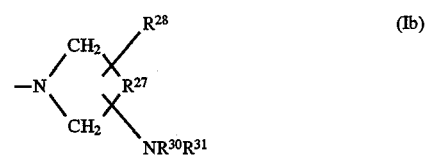

where $R^{27}$ is selected from —$CH_2$—, —$CH_2CH_2$— or —$CH_2CH_2CH_2$—. Alternatively, X and Z when taken together may form —$OCH_2CH_2$— or —$OCH_2O$—, with the proviso that $R^2$ may not be hydrogen.

$R^{28}$ in Formula Ib is selected from hydrogen, halogen, alkyl of from 1 to 6 carbon atoms, halo-substituted alkyl of from 1 to 6 carbon atoms, and spirocycloalkyl of from 5 to 10 carbon atoms.

$R^{30}$ and $R^{31}$ in Formula Ib are each independently selected from the group consisting of hydrogen, acetyl, alkyl, an α-amino acid joined to the nitrogen with an amide linkage, and a polypeptide residue of 2 to 5 amino acids joined to the nitrogen with an amide linkage, with the provisos (a) that when A is O, $R^{30}$ and $R^{31}$ are each independently selected from a peptidyl group of from 1 to 5 amino acids joined to the nitrogen with an amide linkage, and (b) that both $R^{30}$ and $R^{31}$ may not be hydrogen at the same time.

As will be appreciated by those skilled in the art, the pyridyl group at Z described above can be susbtituted or unsubstituted. Suitable substitutents on the pyridine ring include alkyl of from 1 to 6 carbon atoms, halogen, alkanoyl of from 1 to 6 carbon atoms, and alkanoylamido of from 1 to 6 carbon atoms.

DETAILED DESCRIPTION AND PREFERRED EMBODIMENTS

The present invention relates to compounds which have antineoplastic activity and to a method of treating neoplastic diseases. More particularly, the invention relates to a method of treating neoplastic diseases comprising administering to a host animal in need of such treatment a therapeutically effective amount of a compound of the Formula I as described above. In connection with Formula I, the terms below are defined as follows:

The term "α-amino acid" refers to a single amino acid. The amino acids can be naturally occurring amino acids such as valine or glycine, or they may be synthetic alpha-amino acids such as cyclohexylalanine. The amino acids can be either in the L or D configuration or a mixture or the two isomers. If not specified, amino acid substituents are optically active and have the the L configuration.

The term "alkanoyl of from 1 to 6 carbon atoms" refers to a substituent of formula —$C(O)R^{19}$ wherein $R^{19}$ is hydrogen or an alkyl group of 1 to 5 carbons, and includes, for example, acetyl.

The term "alkoxy" refers to an oxygen atom substituted with an alkyl group as defined below. Examples include methoxy, ethoxy and propoxy.

The term "alkyl" refers to a monovalent radical derived from an aliphatic hydrocarbon of from 1 to 6 carbon atoms by removal of one hydrogen atom. Examples include methyl, ethyl and propyl.

The term "alkylamino" refers an amino group which may have one to three alkyl substituents, as defined above. Examples include methylamino, ethylamino, dimethylamino and the like.

The term "aminoalkyl" refers to an amino-substituted alkyl group as defined above. Examples include aminoethyl, aminomethyl and the like.

The term "alkylaminoalkyl" refers to amino groups substituted with one to three alkyl groups, as defined above, including methylamino, ethylamino and propylamino bonded to a alkyl substituent as defined above, as for example N,N-dimethylaminoethyl.

The term "alkylsulfonyl" refers to an alkyl group as defined above bonded to a sulfonyl groups, such as ethylsulfonyl or methylsulfonyl.

The term "carboxy-protecting group" refers to and includes the residue of a carboxylic acid ester group. Such carboxy-protecting groups are well known to those skilled in the art, having been extensively used in the protection of carboxyl groups in the penicillin and cephalosporin fields, as described in U.S. Pat. Nos. 3,840,556 and 3,719,667, which are incorporated herein by reference. In general, such carboxy-protecting groups can be relatively easily cleaved to yield the free carboxy group. Representative protecting groups include $C_1$-$C_8$ alkyl (e.g., methyl, ethyl, tertiary, butyl), substituted alkyl (e.g., dimethylaminoethyl), benzyl and substituted derivatives thereof such as alkoxy and nitrobenzyl groups; also suitable are acyl groups such as pivaloyloxymethyl groups. See for example, T. H. Greene, "Protective Groups in Organic Synthesis", John Wiley and Sons, New York, (1981), which is incorporated herein by reference.

The term "halogen" refers to chloro (Cl), bromo (Br), fluoro (F), and iodo (I) groups.

The term "halo-substituted alkyl" refers to a alkyl group, as defined above, in which at least one hydrogen atom is replaced with a halogen atom. Examples of halo-substituted alkyl of from 1 to 6 carbon atoms include fluoromethyl, trifluormethyl, fluoroethyl and the like.

The term "hydroxy-substituted alkyl" refers to an alkyl group having at least one hydroxyl substituent, as for example hydroxyethyl.

The term "neoplastic diseases" refers to disorders and disease states characterized by abnormal proliferative cell growth, such as leukemias, lymphomas, myelomas, melanoma, sarcomas, blastomas and tumors of the head, thyroid, neck, brain, esophagus, lung, breast, stomach, pancreas, genitourinary tract, and the like. Antineoplastic agents are chemical compounds which are effective in the treatment of any one or more neoplastic disease. Chemotherapy of neoplastic diseases is described in "Goodman and Gilman's The Pharmacological Basis of Therapeutics", seventh edition, A. G. Gilman, et al., eds., pp 1240–1306 (1985), which is incorporated herein by reference.

The term "nitrogen-containing heterocycle" refers to a 4- to 7-atom cyclic group containing one, two, or three heteroatoms selected from S, O or N, at least one heteroatom being nitrogen. The cyclic group may be substituted or unsubstituted, either on a heteroatom or on a carbon atom, as with for example alkyl, halo(alkyl), amino(alkyl), hydroxy-substituted alkyl, hydroxy, halogen, amino, an α-amino acid or a polypeptide of from two to five amino acids. Examples of nitrogen-containing heterocycles include azetidine, pyrrolidine, piperidine, piperazine, morpholine, thiomorpholine and the like.

The term "peptidyl" refers to a group of one or more α-amino acids, as described above, joined by an amide bond.

The term "phenyl" refers to either unsubstituted benzene rings or to benzene rings having one to three non-hydrogen substituents independently selected from the group consisting of halogen, hydroxy, alkoxy, alkyl, hydroxy-substituted alkyl, amino, (alkyl)amino, aminoalkyl and a nitrogen-containing heterocycle, as for example aziridinyl, pyrrolidinyl and the like.

The term "prodrug" refers to compounds that are rapidly transformed in vivo to yield the parent compound of the above formula, as for example by hydrolysis in blood. T. Higuchi and V. Stella provide a thorough discussion of the prodrug concept in "Pro-drugs as Novel Delivery Systems", Volume 14 of the A.C.S. Symposium Series, which is incorporated herein by reference.

The term "spirocycloalkyl" refers to saturated bicyclic hydrocarbons having one carbon common to both rings, including for example spiropentane and spiroheptane.

The term "pharmaceutically acceptable salts, esters and amides" refers to those carboxylate salts, amino acid addition salts, esters and amides of the compounds of Formula I as well as the zwitterionic forms thereof, which are, within the scope of sound medical judgement, suitable for use in contact with the tissues of humans and lower animals without undue toxicity, irritation, allergic response and the like; commensurate with a reasonable benefit/risk ratio; and effective for their intended use.

The term "pharmaceutically acceptable salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. (See, for example, S. M. Berge, et al., "Pharmaceutical Salts," *J. Pharm. Sci.*, 66:1–19 (1977), which is incorporated herein by reference.)

Examples of pharmaceutically acceptable, non-toxic esters of the compounds of Formula I include $C_1$ to $C_6$ alkyl esters wherein the alkyl group is straight or branched chain. Acceptable esters also include $C_5$ to $C_7$ cycloalkyl esters. $C_1$ to $C_4$ alkyl esters are preferred. Esters of the compounds of Formula I may be prepared according to conventional methods.

Examples of pharmaceutically acceptable, nontoxic amides of the compounds of Formula I include amides derived from ammonia, primary $C_1$ to $C_6$ alkyl amines and secondary $C_1$ to $C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$ to $C_3$ alkyl primary amides of Formula I may be prepared according to conventional methods. It is understood that amides of the present invention include amino acid and peptide derivatives.

Preferred compounds of the present invention include those having the structure:

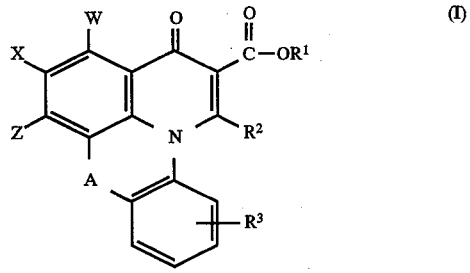

wherein $R^1$, $R^2$, $R^3$, and W are as described, A is O, Z is an amino group or an aliphatic heterocycle, and X is F. Highly preferred compounds include those having the structure as described above in which Z is aminopyrrolidinyl, 2-methyl-4-aminopyrrolidinyl, norvalylaminopyrrolidinyl, alanylaminopyrrolidinyl, alanylalanylaminopyrrolidinyl, norvalylnorvalylaminopyrrolidinyl, alanylnorvalylaminopyrrolidinyl and norvalylalanylaminopyrrolidinyl. It has also been found that compounds wherein at least one of $R^{30}$ and $R^{31}$ is a dipeptidyl group have surprisingly improved aqueous solubility; compounds wherein A is a dipeptidylaminopyrrolidinyl moiety are therefore particularly preferred. Of these, the compound wherein Z is alanylalanylaminopyrrolidinyl is especially preferred.

The following compounds are representative of the preferred compounds of the present invention:

1-(3-aminopyrrolidin-1-yl)-2-fluoro-4-oxo-4H-quino[2,3,4-i,j][1,4]benzoxazine-5-carboxylic acid;

1-(3-aminopyrrolidin-1-yl)-2-fluoro-8-methyl-4-oxo-4H-quino[2,3,4-i,j][1,4]benzoxazine-5-carboxylic acid;

1-(3-acetamidopyrrolidin-1-yl)-2-fluoro-9-nitro-4-oxo-4H-quino[2,3,4-i,j][1,4]benzoxazine-5-carboxylic acid;

1-(3-aminopyrrolidin-1-yl)-2-fluoro-9-methyl-4-oxo-4H-quino[2,3,4-i,j][1,4]benzoxazine-5-carboxylic acid;

1-(3-aminopyrrolidin-1-yl)-2,9-difluoro-4-oxo-4H-quino[2,3,4-i,j][1,4]benzoxazine-5-carboxylic acid;

1-(3-norvalylaminopyrrolidin-1-yl)-2-fluoro-4-oxo-4H-quino[2,3,4-i,j][1,4]benzoxazine-5-carboxylic acid;

1-(3-alanylaminopyrrolidin-1-yl)-2-fluoro-9-methyl-4-oxo-4H-quino[2,3,4-i,j][1,4]benzoxazine-5-carboxylic acid.

1-(3-norvalylaminopyrrolidin-1-yl)-2-fluoro-9-methyl-4-oxo-4H-quino[2,3,4-i,j][1,4]benzoxazine-5-carboxylic acid;

1-(3-norvalylaminopyrrolidin-1-yl)-2-fluoro-8-methyl-4-oxo-4H-quino[2,3,4-i,j][1,4]benzoxazine-5-carboxylic acid;

1-(3-alanylaminopyrrolidin-1-yl)-2-fluoro-8-methyl-4-oxo-4H-quino[2,3,4-i,j][1,4]benzoxazine-5-carboxylic acid.

1-(3-aminopyrrolidin-1-yl)-2-fluoro-4-oxo-4H-quino[2,3,4-i,j][1,4]benzothiazine-5-carboxylic acid;

1-(3-aminopyrrolidin-1-yl)-2-fluoro-8-methyl-4-oxo-4H-quino[2,3,4-i,j][1,4]benzothiazine-5-carboxylic acid;

1-(3-alanylaminopyrrolidin-1-yl)-2-fluoro-4-oxo-4H-quino[2,3,4-i,j][1,4]benzothiazine-5-carboxylic acid.

1-(3-acetamidopyrrolidin-1-yl)-2-fluoro-9-nitro-4-oxo-4H-quino[2,3,4-i,j][1,4]benzothiazine-5-carboxylic acid;

1-(3-aminopyrrolidin-1-yl)-2,9-difluoro-4-oxo-4H-quino[2,3,4-i,j][1,4]benzothiazine-5-carboxylic acid;

1-(3-norvalylaminopyrrolidin-1-yl)-2-fluoro-9-methyl-4-oxo-4H-quino[2,3,4-i,j][1,4]benzothiazine-5-carboxylic acid;

1-(3-aminopyrrolidin-1-yl)-2-fluoro-4-oxo-4H-quino[2,3,4-i,j][1,4]benzothiazine-5-carboxylic acid;

1-(3-alanylaminopyrrolidin-1-yl)-2-fluoro-9-methyl-4-oxo-4H-quino[2,3,4-i,j][1,4]benzothiazine-5-carboxylic acid;

1-(3-norvalylaminopyrrolidin-1-yl)-2-fluoro-8-methyl-4-oxo-4H-quino[2,3,4-i,j][1,4]benzothiazine-5-carboxylic acid;

1-(3-alanylaminopyrrolidin-1-yl)-2-fluoro-8-methyl-4-oxo-4H-quino[2,3,4-i,j][1,4]benzothiazine-5-carboxylic acid;

1H,7H-pyrido[3,2,1-de]acridine-3-one-5-fluoro-6-(3-aminopyrrolidin-1-yl)-2-carboxylic acid;

1-(3-aminopyrrolidin-1-yl)-8,10-dimethyl-2-fluoro-4-oxo-4H-quino[2,3,4-i,j][1,4]benzoxazine-5-carboxylic acid;

1-((3S)-3-aminopyrrolidin-1-yl)-2-fluoro-4-oxo-4H-quino[2,3,4-i,j][1,4]benzoxazine-5-carboxylic acid;

1-((3R)-3-aminopyrrolidin-1-yl)-2-fluoro-4-oxo-4H-quino[2,3,4-i,j][1,4]benzoxazine-5-carboxylic acid;

1-((3S)-3-aminopyrrolidin-1-yl)-2-fluoro-9-methyl-4-oxo-4H-quino[2,3,4-i,j][1,4]benzoxazine-5-carboxylic acid;

1-((3R)-3-aminopyrrolidin-1-yl)-2-fluoro-9-methyl-4-oxo-4H-quino[2,3,4-i,j][1,4]benzoxazine-5-carboxylic acid;

2-fluoro-1-(3-norvalylaminopyrrolidin-1-yl)-8-methyl-4-oxo-4H-quino[2,3,4-i,j][1,4]benzoxazine-5-carboxylic acid;

1-(3-aminopyrrolidin-1-yl)-8-t-butyl-2-fluoro-4-oxo-4H-quino[2,3,4-i,j][1,4]benzoxazine-5-carboxylic acid;

1-(3-aminopyrrolidin-1-yl)-2,3-difluoro-4-oxo-4H-quino[2,3,4-i,j][1,4]benzoxazine-5-carboxylic acid;

2,3-difluoro-1-(3-norvalylaminopyrrolidin-1-yl)-4-oxo-4H-quino[2,3,4-i,j][1,4]benzoxazine-5-carboxylic acid;

2-fluoro-1-((3R)-3-norvalylaminopyrrolidin-1-yl)-4-oxo-4H-quino[2,3,4-i,j][1,4]benzoxazine-5-carboxylic acid;

2-fluoro-1-((3S)-3-norvalylaminopyrrolidin-1-yl)-4-oxo-4H-quino[2,3,4-i,j][1,4]benzoxazine-5-carboxylic acid;

2-fluoro-9-methyl-1-((3R)-3-norvalylaminopyrrolidin-1-yl)-4-oxo-4H-quino[2,3,4-i,j][1,4]benzoxazine-5-carboxylic acid;

1-(3-aminopyrrolidin-1-yl)-8-ethylsulfonyl-2-fluoro-4-oxo-4H-quino[2,3,4-i,j][1,4]benzoxazine-5-carboxylic acid;

8-ethylsulfonyl-2-fluoro-1-(3-norvalaminopyrrolidin-1-yl)-4-oxo-4H-quino[2,3,4-i,j][1,4]benzoxazine-5-carboxylic acid;

1-(3-aminopyrrolidin-1-yl)-2-fluoro-5-(1-morpholinocarbonyl)-4-oxo-4H-quino[2,3,4-i,j][1,4]benzoxazine;

1-(3-aminopyrrolidin-1-yl)-2-fluoro-4-oxo-4H-quino[2,3,4-i,j][1,4]benzoxazine-5-(N-2,4-difluorphenyl)carboxamide;

1-((2S,4S)-4-amino-2-methylpyrrolidin-1-yl)-8,10-dimethyl-2-fluoro-4-oxo-4H-quino[2,3,4-i,j][1,4]benzoxazine-5-carboxylic acid;

1-((2S,4S)-4-amino-2-methylpyrrolidin-1-yl)-2-fluoro-8-methyl-4-oxo-4H-quino[2,3,4-i,j][1,4]benzoxazine-5-carboxylic acid;

1-((2S,4S)-4-amino-2-methylpyrrolidin-1-yl)-2-fluoro-4-oxo-4H-quino[2,3,4-i,j][1,4]benzoxazine-5-carboxylic acid;

1-(3-aminopyrrolidin-1-yl)-2-fluoro-8,9-methylenedioxy-4-oxo-4H-quino[2,3,4-i,j][1,4]benzoxazine-5-carboxylic acid;

ethyl 1-(3-aminopyrrolidin-1-yl)-2-fluoro-8,9-methylenedioxy-4-oxo-4H-quino[2,3,4-i,j][1,4]benzoxazine-5-carboxylate;

3-amino-1-(3-aminopyrrolidin-1-yl)-2-fluoro-4-oxo-4H-quino[2,3,4-i,j][1,4]benzoxazine-5-carboxylic acid;

1-(3-alanylalanylaminopyrrolidin-1-yl)-2-fluoro-4-oxo-4H-quino[2,3,4-i,j][1,4]benzoxazine-5-carboxylic acid;

1-(3-norvalylnorvalylaminopyrrolidin-1-yl)-2-fluoro-4-oxo-4H-quino[2,3,4-i,j][1,4]benzoxazine-5-carboxylic acid;

1-(3-alanylnorvalylaminopyrrolidin-1-yl)-2-fluoro-4-oxo-4H-quino[2,3,4-i,j][1,4]benzoxazine-5-carboxylic acid;

1-(3-norvalylalanyiaminopyrrolidin-1-yl)-2-fluoro-4-oxo-4H-quino[2,3,4-i,j][1,4]benzoxazine-5-carboxylic acid;

and pharmaceutically acceptable salts of any of the foregoing compounds. These and other compounds of the present invention are found to have in vitro and in vivo activity against both human and murine tumor cell lines including leukemia, melanoma, and lung, colon and ovarian carcinomas, as well as having activity against some tumor cell lines known to be resistant to ADRIAMYCIN (doxorubicin hydrochloride), an antineoplastic agent currently in use.

The chiral centers of the compounds of the present invention may have either the R, S, or racemic configuration. Methods of resolution of the enantiomeric forms of these compounds are well known to those skilled in the art. For example, J. March provides a thorough discussion of resolution methods in "Advanced Organic Chemistry", John Wiley and Sons, Inc, New York, (1985), which is incorporated herein by reference.

The present invention also provides pharmaceutical compositions which comprise one or more of the compounds of the invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, as for example by filtration through a bacterial-retaining filter, or by incorporating sterilizing agents in the form of sterile solid compositions which can be dissolved or dispersed in sterile water or other stedle injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract or, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are well-known in the art. See, for example, Prescott, Ed., *Methods in Cell Biology*, Volume XIV, Academic Press, New York, N.Y. (1976), p. 33 et seq., which is incorporated herein by reference Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

Dosage regimens must be titrated to the particular neoplasm, the condition of the patient and the response obtained, but generally dosage levels of about 0.1 to about 750 mg/kg body weight, more preferably of about 0.25 to about 500 mg/kg body weight, and most preferably about 0.5 to about 300 mg of active compound per kilogram of body weight per day are administered orally or intravenously to a mammalian patient. If desired, the effective daily dose may be divided into multiple doses for purposes of administration, e.g., two to four separate doses per day.

In general, the compounds of the present invention are synthesized as reported by D. Chu and R. Maleczka in the *J. Heterocyclic Chem.* 24: 453 (1987) and by D. Chu in U.S. Pat. Nos. 4,607,032, 4,529,725 and 4,528,285, which are incorporated herein by reference, or according to reaction Schemes I to IV presented below, in which R, $R^1$ and $R^2$ are lower alkyl and $R^3$ is as defined above in connection with Formula I.

For the preparation of the compounds of Formula I which are α-amino acids or peptide derivatives of amine groups in Z, the condensation of the amino group with amino acids and peptides may be effected in accordance with conventional condensation methods such as the azide method, the mixed acid anhyddde method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxybenzotriazole) method and the like. Classical methods for amino acid condensation reactions are described in "Peptide Synthesis" Second Edition, M. Bodansky, Y. S. Klausner and M. A. Ondetti (1976), which is incorporated herein by reference. It is contemplated that the amino acid coupling reaction could be carried out before or after the amino-containing group is incorporated into the compound by displacement of the 7-fluorine atom of the appropriate intermediate.

As in conventional peptide sysnthesis, branced chain amino and carboxyl groups at alpha and omega positions in amino acids may be protected and deprotected if necessary. The protecting groups for amino groups which can be used involve, for example, benzyloxycarbonyl (Z), o-chlorobenzyloxycarbonyl ((2-Cl)Z)), p-nitrobenzyloxycarbonyl (Z(NO₂)), p-methoxybenzyloxycarbonyl (Z(OMe)), t-amyloxycarbonyl (Aoc), isobornealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt) and dimethylphosphino-thioyl (Mpt).

The examples for protecting groups for carboxyl groups involve, for example, benzyl ester (OBzl), cyclohexyl ester, 4-nitrobenzyl ester (OBzlNO₂), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (NG) in arginine may be protected with nitro, p-toluenesulfonyl (Tos), benzyloxycarbonyi (Z), adamantyloxycarbonyl (Adoc), p-rnethoxybenzenesulfonyl, 4-methoxy-2,6-dimethyl-benzenesulfonyl (Mts) and the like, and the thiol group in cysteine may be protected with benzyl, p-methoxybenzyl, triphenylbenzyl, acetomidomethyl, ethylcarbamyl, 4-methylbenzyl (4-MeBzl), 2,4,6-trimethylbenzyl (Tmb) and the like, and the hydroxy group in serine may be protected with benzyl (Bzl), t-butyl, acetyl, tetrahydropyranyl (THP) and the like.

Compounds of this invention can be prepared by the reaction (described by Chu in U.S. Pat. No. 4,607,032) beginning with the compounds of Formula II as shown below, wherein X is halogen and $R^2$ and Z are as previously described, or by the reactions shown in schemes IV or V. The preparation of compounds of Formula II is shown in schemes I, II and III, below.

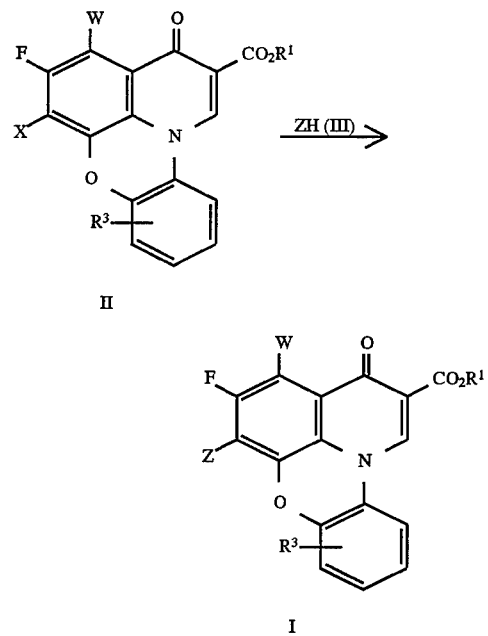

The reaction may be performed by heating a compound of the Formula II with an amine of Formula III at a temperature of from 20° C. to 200°, and preferably from 70° C. to 150° C., in the presence of a suitable organic polar solvent such as dimethysulfoxide, sulfolane, dimethylformamide, dimethylacetamide, 1-methyl-2-pyrrolidone or water. It is desirable to carry out the reaction in the presence of an acid acceptor such as triethylamine, potassium carbonate and the like at a molar ratio of 1.0 to 1.02 mole of the acid receptor per mole of compound of Formula II. The amine III can also be used as acid acceptor in which 2 or more molar excess of this reagent may be used.

Scheme I

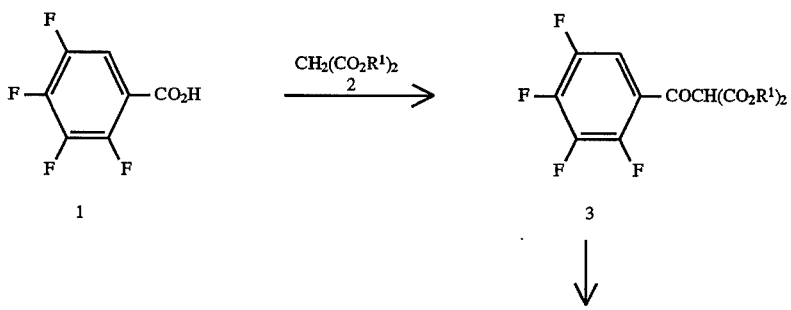

-continued
Scheme I
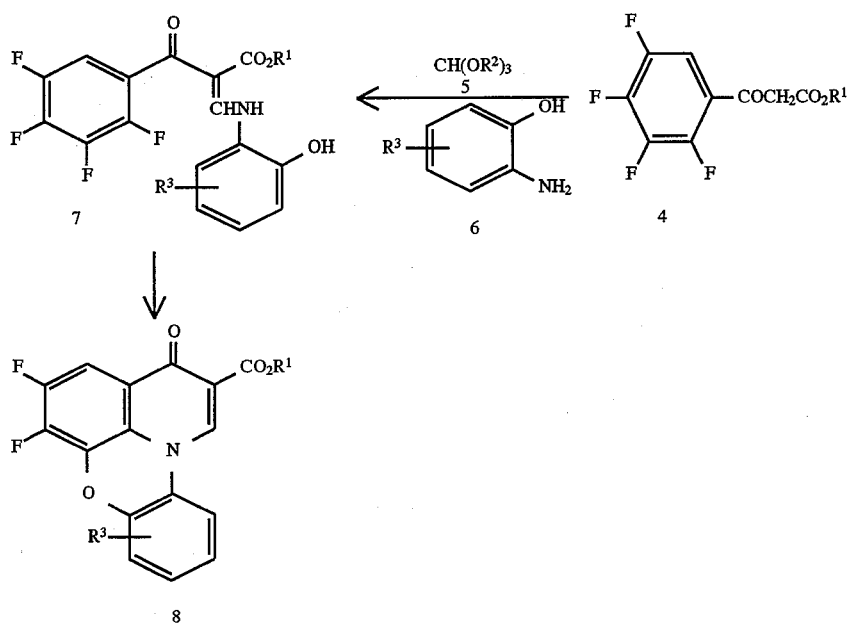
Scheme II
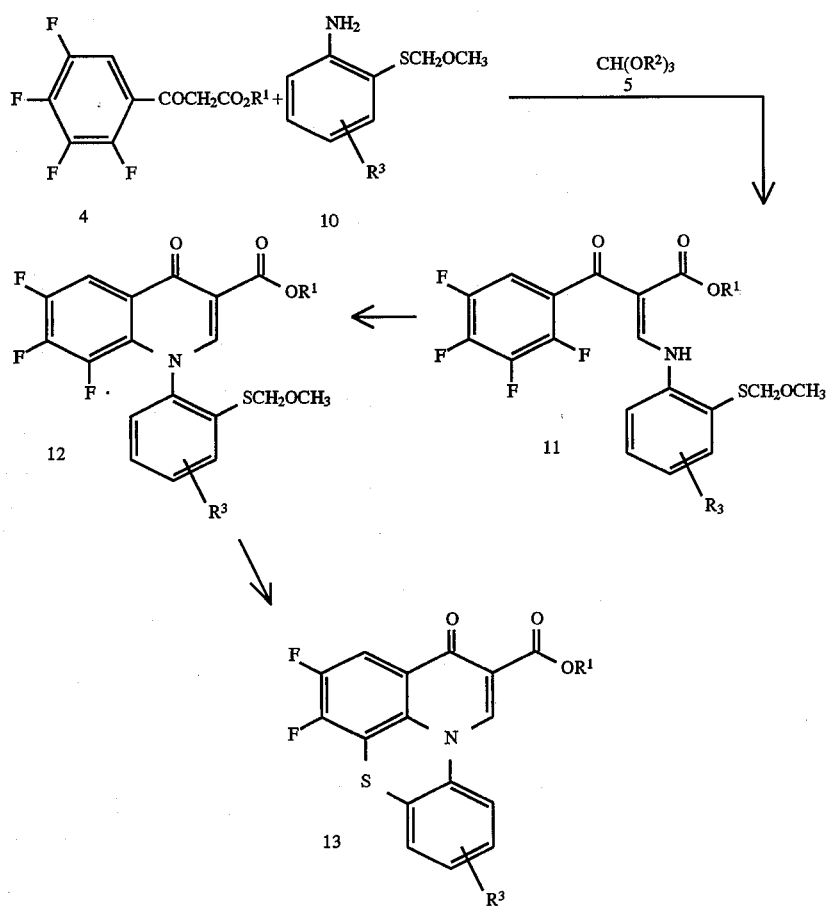

5,624,924
Scheme III
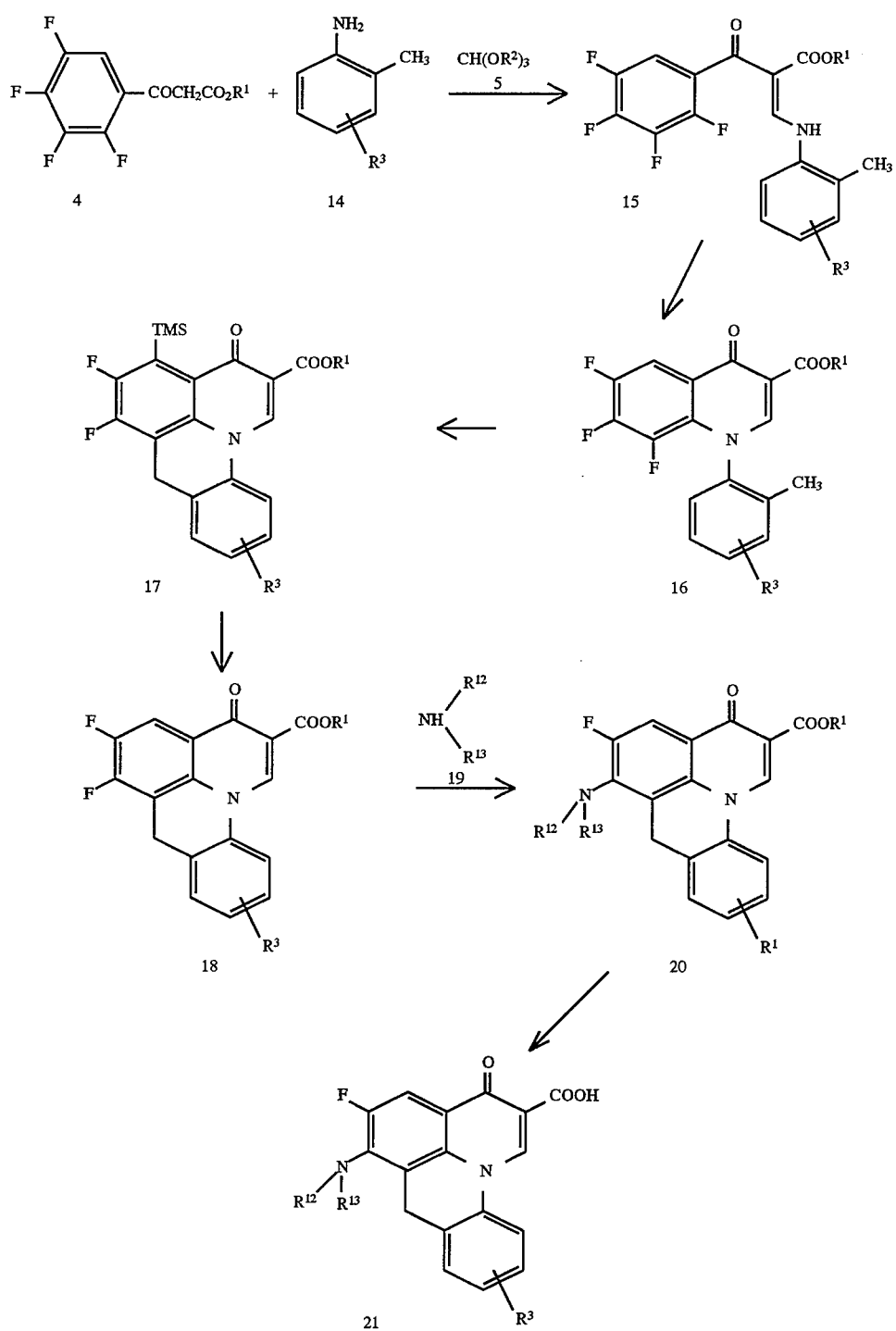

Scheme IV
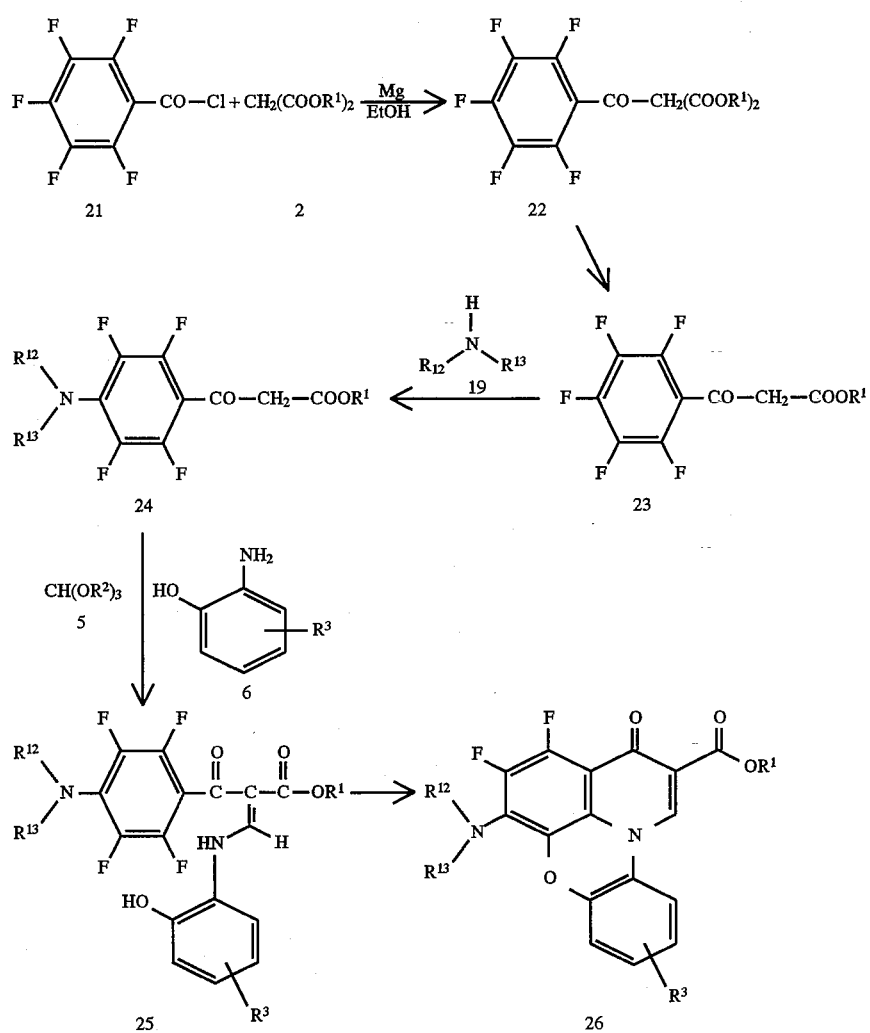
Scheme V
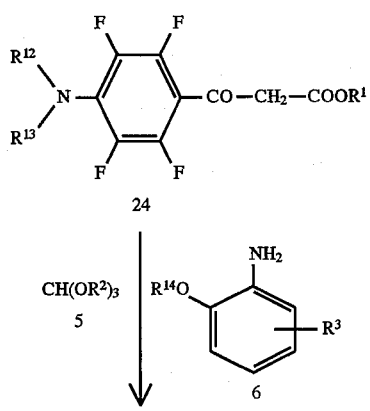

-continued
Scheme V

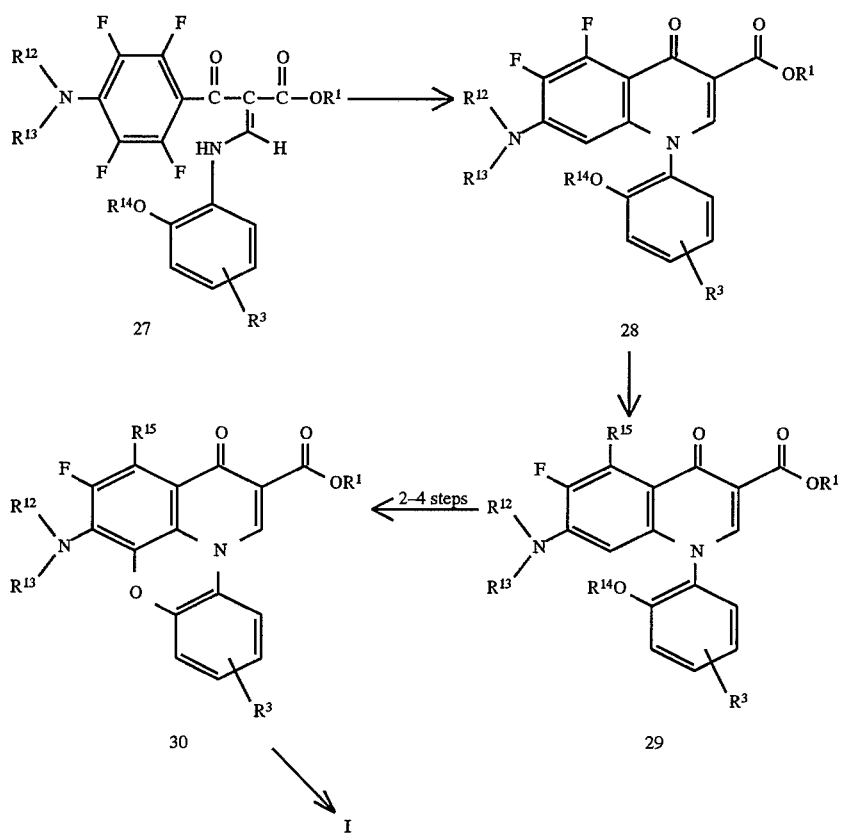

Scheme I

According to the foregoing reaction scheme 2,3,4,5-tetrafluorobenzoic acid (1) is treated with thionyl chloride to produce the corresponding acid chloride which is displaced with a dialkyl malonate, preferably diethyl malonate (2) to yield the diester (3). The diester (3) is then treated with p-toluenesulfonic acid to yield the 2,3,4,5-tetrafluorobenzoylacetate (4). The ester is then treated with a trialkyl orthoformate, preferably triethylorthoformate, (5)in acetic anhydride, followed by reaction with a substituted or unsubstituted O-hydroxyaniline (6) in methylene chloride to give the ethyl 3-(2-hydroxyanilino)-2-(2,3,4,5-tetrafluorobenzoyl)acrylate (7). This enaminoketoester (7) is cyclized in the presence of a suitable base, such as sodium bicarbonate, and an aprotic solvent such as dimethylformamide (DMF) at 100° C. to give ethyl 1,2-difluoro-4-oxo-4H-quino[2,3,4-i,j][1,4]benzoxazine-5-carboxylate (8).

Scheme II

According to the foregoing reaction scheme II, the b-ketoester (4), is treated with a trialkyl orthoformate (5) in acetic anhydride, followed by reaction with a substituted or unsubstituted 2-methoxymethylthioaniline (10)in an appropriate solvent, preferably methylene chloride or tetrahydofuran, and may be conducted at room or suitable elevated temperature, to obtain the enamino-ketoester (11). The enamino-ketoester (11)is then cyclized, such as by treatment with a strong base, preferably sodium hydride, to obtain the 1,4-dihydro-4-oxo-quinoline-3-carboxylic acid ester (12). Cyclization is conducted in the presence of an aprotic solvent, such as dimethoxyethane, dimethylformamide, tetrahydrofuran, or chlorobenzene, and is preferably conducted at temperatures of about 20° C. to about 145° C., and more preferably at the reflux temperature of the solvent employed. The methoxymethylthio ether moiety of (11) is then removed by strong mineral acid or by boron trichloride and is followed by cyclization with a strong base, preferably sodium hydride to yield the ester ($R^1$=lower alkyl, 13) which upon acid or base hydrolysis yields the free acid ($R^1$=H).

Scheme III

According to the foregoing reaction scheme III, the b-ketoester (4), is treated with a trialkyl orthoformate (5) in acetic anhydride followed by reaction with a substituted or unsubstituted 2-methylaniline (14) as described in scheme II to obtain the enamino-ketoester (15). The enamino-ketoester (15)is then cyclized, such as by treatment with a strong base, preferably sodium hydride, to obtain the 1,4-dihydro-4-oxo-quinoline-3-carboxylic acid ester (16) as described above. Further cyclization of the 1,4-dihydro-4-oxo-quinoline-3-carboxylic acid ester (16) to the TMS-protected pyrido-acridine-1-one (17) is accomplished by treatment first with n-butyllithium, followed by treatment with trimethylsilyl chloride (TMS-Cl) and sec-butyllithium in tetrahydrofuran or tetrahydofuran in the presence of tetramethylethyl-diamine (TMEDA). The trimethylsilyl moiety is removed from (16) by treatment with tetrabutylammonium fluoride or cesium fluoride in the presence of dimethylformamide and water to obtain the pyrido-acridine-3-one (18). Amination of (18) may be performed by reaction with an amine of formula (19), wherein $R^{12}$ and $R^{13}$ are as described above with any amino or hydroxyl groups protected by a suitable protecting group, at a temperature of 20° C. to 200° C. in the presence of a suitable organic polar solvent, such as dimethylsulfoxide or sulfolane to obtain the ester (R=lower alkyl, 20), which upon acid or base hydrolysis of any protecting groups and the ester group yields the free acid (21)

Scheme IV

According to the foregoing reaction scheme IV, 2,3,4,5, 6-pentafluorobenzoyl chloride is reacted with a dialkyl malonate, preferably diethyl malonate to yield the diester (22). The diester (22)is then treated with p-toluenesulfonic acid to yield the 2,3,4,5,6-pentafluorobenzoylacetate (23). Amination of (23) may be performed by reaction with an amine of formula (19), wherein $R^{12}$ and $R^{13}$ are as described above with any amino or hydroxyl groups protected by a suitable protecting group, at a temperature of 20° C. to 200° C. in the presence of a suitable organic polar solvent, such as dimethylsulfoxide or sulfolane to obtain the beta-ketoester ($R^1$=lower alkyl, (24). The beta-ketoester (24)is then treated with a trialkyl orthoformate, preferably triethylorthoformate, in acetic anhydride, followed by reaction with a substituted or unsubstituted O-hydroxyaniline or hydroxy-protected O-hydroxyaniline (6) in methylene chloride to give the ethyl 3-(2-hydroxyanilino)-2-(4-amino-2,3, 5,6-pentafluorobenzoyl)acrylate (25). This enaminoketoester (25) is cyclized in the presence of a suitable base, such as sodium bicarbonate, and an aprotic solvent such as dimethylformamide (DMF) at 100° C. to give the appropriately substituted ethyl 2,3-difluoro-4-oxo-4H-quino[2,3,4-i, j][1,4]benzoxazine-5-carboxylate (26), which upon hydrolysis of any protecting groups and the ester group yields the free acid (26)

Scheme V

According to the foregoing reaction scheme V, the beta-ketoester (24) is treated with a trialkyl orthoformate, preferably triethylorthoformate, in acetic anhydride, followed by reaction with a substituted or unsubstituted hydroxy-protected O-hydroxyaniline (6) in methylene chloride to give an enaminoketoester (27). The first ring is then is cyclized in the presence of a suitable base, such as sodium bicarbonate, and an aprotic solvent such as dimethylformamide (DMF) at 100° C. to give compound (28). This compound is then reacted with $R^{15}H$ where $R^{15}$ is WH, where W is as described above, or $R^{16}$—N—H where $R^{16}$ is a nitrogen protecting group, as for example benzyl, to give the compound (29). The protecting group is removed, for example by hydrogenolysis of the benzyl group to give the free amine. The free amine is then reprotected with a protecting group not requiring hydrogenolysis for removal, for example, acetyl or t-butyloxycarbonyl (boc), the protecting group is removed from the phenolic hydroxyl group by selective hydrolysis, for example with pyridine hydrochloride, TFA, or boron tribromide and ether and the second ring is closed by reaction in the presence of a suitable base, such as sodium bicarbonate, and an aprotic solvent such as dimethylformamide (DMF) at 100° C. to give compound (30) Protecting groups are then removed by acid or base hydrolysis to give the appropriately substituted compound of Formula I.

The foregoing may be better understood from the following examples, which are presented for the purpose of illustration and not intended to limit the scope of the inventive concept.

EXAMPLE 1

Ethyl 2,3,4,5-tetrafluorobenzoylacetate

Step 1: Ethyl 2,3,4,5-Tetrafluorobenzoyldiacetate

To 12.16 g (0.50 mol) of magnesium powder was added 50 mL of ethanol and 1 mL of $CCl_4$, followed by dropwise under anhydrous conditions a solution of 80.09 g (0.50 mol) of malonic acid diethyl ester in 300 mL of ethanol. After the end of the addition, the mixture was heated at reflux for 4 hours, then stirred at room temperature overnight. The solvent was then removed, the residual ethanol was removed by azeotropic distillation with toluene (3×), then the residue was redissolved in dry toluene.

2,3,4,5-Tetrafluorobenzoic acid (100 g, 0.515 mol) was added to 300 mL of thionyl choloride. After refluxing for 3 hours, the reaction mixture was evaporated to dryness and the resulting acid chloride was dissolved in toluene.

The acid chloride solution was then added in a dropwise manner to the magnesium salt solution. Additional solvent was added and the mixture was stirred at room temperature overnight. The mixture was then poured into 600 mL of 10% sulfuric acid solution and diluted with 600 mL of chloroform. The organic layer was dried over anhydrous magnesium sulfate and evaporated to yield the 169.8 g of the diester.

Step 2: Ethyl 2,3,4,5-tetrafluorobenzoylacetate

The diester from step 1 (169.8 g, 0.505 mol) was suspended in water and p-toluenesulfonic acid (730 mg) added. The suspension was stirred rapidly, refluxed for three hours, and allowed to cool to room temperature. After cooling, the solution was extracted with chloroform and washed with 5% sodium bicarbonate solution. The organic layer was dried over anhydrous magnesium sulfate, filtered and evaporated to dryness yielding a golden colored syrup. The product was azetroped several times with methylene chloride to yield 132.7 g of ethyl 2,3,4,5-tetrafluorobenzolyacetate. This was crystallized from pentane, yielding 119.43 g.

EXAMPLE 2

Ethyl-3-(2-hydroxy-5-nitroanilino)-2-(2,3,4,5-tetrafluorobenzoyl)acrylate

Ethyl 2,3,4,5-tetrafluorobenzoylacetate, from Example 1, step 2 above, was reacted with 2-hydroxy-5-nitroaniline by a method similar to that described in the J. Heterocycl. Chem., 24: 453 (1987) to afford the title compound, m.p. 222° C.; MS M/Z: 429 (M+H); IR(KBr) 1630, 1675 $cm^{-1}$; NMR (DMSO) d: 1.02 (m, 3H), 4.05 (m 2H), 7.13 (m, 1H), 7.55 (m, 1H), 8.02 (m, 1H), 8.50 (m, 1H), 8.77 (m, 1H), 11.25 (m, 1H), 12.11 (m, 1H). Analysis calculated for C, 50.47; H, 2.83; N, 6.54. Found C, 50.12; H, 2.80; N, 6.47.

EXAMPLE 3

Ethyl 1,2-difluoro-4-oxo-4H-quino[2,3,4-i,j][1,4] benzoxazine-5-carboxylate

Ethyl-3-(2-hydroxyanilino)-2-(2,3,4,5-tetrafluorobenzoyl)acrylate (19.92 g, 0.052 mol) was dissolved in 200 mL of dimethylformamide (DMF) and sodium bicarbonate powder (13.1 g, 0.156 mol) was added. The suspension was immersed in a pre-heated oil bath at 100° C. and heated for 2 hours. The mixture was then allowed to cool slightly, diluted with chloroform, and filtered. The flitrate was evaporated to a solution of DMF and allowed to stand at room temperature overnight. After standing, the solution was co-distilled with toluene to yield a light yellow-colored solid. The solid was dried, dissolved in chloroform, and washed with 1N hydrochloric acid and 5% potassium carbonate solution. The organic layer was dried over anhydrous magnesium sulfate, filtered and evaporated to a light yellow-colored solid. Diethyl ether was added to the solid and the mixture allowed to stand for several hours. The solid was then removed by filtration, washed with fresh diethyl ether, and dried at 70° C. overnight to yield 16.00 g of ethyl 1,2-difluoro-4-oxo-4H-quino[2,3,4-i,j][1,4]benzoxazine-5-carboxylate.

EXAMPLE 4

1-(3-aminopyrrolidin-1-yl)-2-fluoro-8-methyl-4-oxo-4H-quino[2,3,4-i,j][1,4]benzoxazine-5-carboxylic acid hydrochloride Step 1: Ethyl 1,2-difluoro-8-methyl-4-oxo-4H-quino[2,3,4-i,j][1,4]benzoxazine-5-carboxylate Ethyl-3-(2'-hydroxy, 5'-methylanilino)-2-(2,3,4,5-tetrafluorobenzoyl)acrylate was prepared by a method similar to that described in the *J. Heterocycl. Chem.*, 24:453 (1987) from ethyl 2,3,4,5-tetrafluorobenzoylacetate. m.p. 202°–3° C.; MS M/Z: 398 (M+H); IR (CDCl$_3$) 1630, 1670 cm$^{-1}$; NMR (CDCl$_3$) d: 1.15 (m, 3H), 2.35 (s, 3H), 4.15 (m, 2H), 5.42 (s, 1H), 6.77 (m, 1H), 6.90 (m, 1H), 7.10 (m, 1H), 7.18 (s, 1H), 8.65 (d, 1H), 12.7 (m 1H). Analysis calculated for C, 57.43; H,3.80; N, 3.53. Found: C, 57.19; H, 3.86; N, 3.53.

The product of the above reaction was then cyclized in the presence of sodium bicarbonate and dimethylformamide (DMF) as described in Scheme 1 to yield ethyl 1,2-difluoro-8-methyl-4-oxo-4H-quino[2,3,4-i,j][1,4]benzoxazine-5-carboxylate. m.p. 200°–1° C.; MS M/Z: 358 (M+H); IR (KBr) 1690, 1730 cm$^{-1}$; NMR (DMSO) d: 1.32 (m, 3H), 2.35 (s, 3H), 4.29 (m, 2H), 7.11 (m, 1H), 7.18 (m, 1H), 7.56 (m, 1H), 7.80 (s, 1H), 9.02 (s, 1H). Analysis calculated for C, 63.86; H, 3.67; N, 3.92. Found: C, 63.38; H, 3.69; N, 3.87.

Step 2: Ethyl 1-(3-acetamidopyrrolidin-1-yl)-2-fluoro-8-methyl-4-oxo-4H-quino[2,3,4-i,j][1,4]benzoxezine-5-carboxylate Ethyl 1,2-difluoro-8-methyl-4-oxo-4H-quino[2,3,4-i,j][1,4]benzoxazine-5-carboxylate was then reacted as described in U.S. Pat. No. 4,607,032 to yield ethyl 1-(3-acetamidopyrrolidin-1-yl)-2-fluoro-8-methyl-4-oxo-4H-quino[2,3,4-i,j][1,4]benzoxazine-5-carboxylate. m.p. 207°–10° C.; MS M/Z: 466 (M+H); IR (KBr) 1660, 1685, 1725 cm$^{-1}$; NMR (CDCl$_3$) d: 1.43 (m, 3H), 2.05 (m, 2H), 2.15 (s, 3H), 2.48 (s, 3H), 3.52 (m, 2H), 3.96 (m, 2H), 4.42 (m, 2H), 4.62 (m, 1H), 6.83 (m, 1H), 6.92 (m, 1H), 7.03 (m, 1H), 7.10 (m, 1H), 7.42 (m, 1H), 8.47 (s, 1H). Analysis calculated with 1/2 mol of H$_2$O for C, 63.28; H, 5.31; N, 8.86. Found: C, 63.70; H, 5.26; N, 8.84.

Step 3: 1-(3-aminopyrrolidin-1-yl)-2-fluoro-8-methyl-4-oxo-4H-quino[2,3,4-i,j][1,4]benzoxazine-5-carboxylic acid hydrochloride Ethyl 1-(3-acetamidopyrrolidin-1-yl)-2-fluoro-8-methyl-4-oxo-4H-quino[2,3,4-i,j][1,4]benzoxazine-5-carboxylate was then deprotected by a method similar to that described in the *J. Heterocycl. Chem.*, 24:453 (1987) to yield the title compound.

EXAMPLE 5

Ethyl 1-(3-acetamidopyrrolidin1-yl)-2-fluoro-9-nitro-4-oxo-4H-quino[2,3,4-i,j][1,4]benzoxazine-5-carboxylate Step 1: Ethyl 1,2-fluoro-9-nitro-4-oxo-4H-quino[2,3,4-i,j][1,4]benzoxazine-5-carboxylate Ethyl-3-(2-hydroxy-4-nitroanilino)-2-(2,3,4,5-tetrafluorobenzoyl)acrylate was prepared by a method similar to that described in the *J. Heterocycl. Chem.*, 24:453 (1987) from ethyl 2,3,4,5-tetrafluorobenzoylacetate. m.p. 225° C.; MS M/Z: 429 (M+H); IR (KBr) 1640, 1660 cm$^{-1}$; NMR (DMSO) d: 1.05 (m, 3H), 4.07 (m, 2H), 7.57 (m, 1H), 7.80 (m, 2H), 7.93 (m, 1H), 8.70 (m, 1H), 11.70 (m, 1H). Analysis calculated for C, 50.47; H, 2.83; N, 6.54. Found C, 50.46; H, 2.87; N, 6.53.

The product of the above reaction was then cyclized in the presence of sodium bicarbonate and dimethylformamide (DMF) as described in Scheme 1 to yield ethyl 1,2-difluoro-8-nitro-4-oxo-4H-quino[2,3,4-i,j][1,4]benzoxazine-5-carboxylate. m.p. 255°–8° C.; MS M/Z: 389 (M+H); IR (KBr) 1700, 1730 cm$^{-1}$; NMR (DMSO) d: 1.32 (m, 3H), 4.30 (m, 2H), 7.65 (m, 1H), 8.08 (m, 1H), 8.20 (m, 1H), 9.11 (s, 1H). Analysis calculated for C, 55.68; H, 2.60; N, 7.22. Found: C, 55.48; H, 2.50; N, 7.32.

Step 2: Ethyl 1-(3-acetamidopyrrolidin-1-yl)-2-fluoro-9-nitro-4-oxo-4H-quino[2,3,4-i,j][1,4]benzoxazine-5-carboxylate Ethyl 1,2-difluoro-9-nitro-4-oxo-4H-quino[2,3,4-i,j][1,4]benzoxazine-5-carboxylate was then reacted as described in U.S. Pat. No. 4,607,032 to yield ethyl 1-(3-acetamidopyrrolidin-1-yl)-2-fluoro-9-nitro-4-oxo-4H-quino[2,3,4-i,j][1,4]benzoxazine-5-carboxylate. m.p. 256°–9° C.; MS M/Z: 497 (M+H); IR (KBr) 1660, 1695, 1720 cm$^{-1}$; NMR (DMSO-d6) d: 1.31 (m, 3H), 1.80 (m, 1H), 1.85 (s, 3H), 2.10 (m, 1H), 3.48 (m, 1H), 3.72 (m, 1H), 3.84 (m, 1H),3.89 (m, 1H), 4.26 (m, 3H), 7.35 (m, 1H), 8.00 (m, 3H), 8.15 (m, 1H), 8.88 (m, 1H). Analysis calculated for C, 58.06; H, 4.26; N, 11.29. Found: C, 57.81; H, 4.32; N, 11.28.

EXAMPLE 6

1-(3-aminopyrrolidin-1-yl)-2-fluoro-9-methyl-4-oxo-4H-quino[2,3,4-i,j][1,4]benzoxazine-5-carboxylic acid hydrochloride Step 1: Ethyl 1,2-difluoro-9-methyl-4-oxo-4H-quino[2,3,4-i,j][1,4]benzoxazine-5-carboxylate Ethyl-3-(2'-hydroxy, 4'-methylanilino)-2-(2,3,4,5-tetrafluorobenzoyl)acrylate was prepared according by a method similar to that described in the *J. Heterocycl, Chem.*, 24:453 (1987) from ethyl 2,3,4,5-tetrafluorobenzoylacetate. m.p. 182°–3° C.; MS M/Z: 398 (M+H); IR (KBr) 1630, 1670 cm$^{-1}$; NMR (DMSO) d: 1.05 (m, 3H), 2.25 (s, 3H), 4.03 (m, 2H), 6.73 (m, 1H), 6.80 (s, 1H), 7.50 (m, 2H), 8.67 (m, 1H), 10.53 (m, 1H), 12.7 (m 1H). Analysis calculated for C, 57.43; H,3.80; N, 3.53. Found C, 57.45; H, 3.83, N, 3.52.

The product of the above reaction was then cyclized in the presence of sodium bicarbonate and dimethylformamide (DMF) as described in Scheme 1 to yield ethyl 1,2-difluoro-9-methyl-4-oxo-4H-quino[2,3,4-i,j][1,4]benzoxazine-5-carboxylate. m.p. 183°–4° C.; MS M/Z: 358 (M+H); IR (KBr) 1700, 1735 cm$^{-1}$; NMR (DMSO) d: 1.32 (m, 3H), 2.31 (s, 3H), 4.28 (m, 2H), 7.08 (m, 1H), 7.14 (m, 1H), 7.60 (m, 1H), 7.83 (m, 1H), 9.00 (s, 1H). Analysis calculated for C, 63.86; H, 3.67; N, 3.92. Found: C, 63.39; H, 3.69; N, 3.87.

Step 2: Ethyl 1-(3-acetamidopyrrolidin-1-yl)-2-fluoro-9-methyl-4-oxo-4H-quino[2,3,4-i,j][1,4]benzoxazine-5-carboxylate Ethyl 1,2-difluoro-9-methyl-4-oxo-4H-quino[2,3,4-i,j][1,4]benzoxazine-5-carboxylate was then reacted as described in U.S. Pat. No. 4,607,032 to yield ethyl 1-(3-acetamidopyrrolidin-1-yl)-2-fluoro-9-methyl-4-oxo-4H-quino[2,3,4-i,j][1,4]benzoxazine-5-carboxylate. m.p. 230°–2° C.; MS M/Z: 466 (M+H); IR (KBr) 1670, 1720 cm$^{-1}$; NMR (DMSO-d6) d: 1.31 (m, 3H), 1.80 (m, 1H), 1.83

(s, 3H), 2.10 (m, 1H), 2.30 (s, 3H), 3.42 (m, 1H), 3.68 (m, 1H), 3.78 (m, 1H), 3.86 (m, 1H), 4.25 (m, 3H), 7.02 (m, 2H), 7.30 (m, 1H), 7.65(m, 1H), 8.15 (m, 1H), 8.80 (s, 1H). Analysis calculated with 1/2 mol of $H_2O$ for C, 63.28; H, 5.31; N, 8.86. Found: C, 63.19; H, 5.26; N, 8.81.

Step 3: 1-(3-aminopyrrolidin-1-yl)-2-fluoro-9-methyl-4-oxo-4H-quino[2,3,4-i,j][1,4]benzoxazine-5-carboxylic acid hydrochloride Ethyl 1-(3-acetamidopyrrolidin-1-yl)-2-fluoro-9-methyl-4-oxo-4H-quino[2,3,4-i,j][1,4]benzoxazine-5-carboxylate was then deprotected by a method similar to that described in the *J. Heterocycl. Chem.*, 24:453 (1987) to yield 1-(3-aminopyrrolidin-1-yl)-2-fluoro-9-methyl-4-oxo-4H-quino[2,3,4-i,j][1,4]benzoxazine-5-carboxylic acid hydrochloride. m.p. >290° C.; MS M/Z: 396 (M+H); IR (KBr) 1630, 1720 $cm^{-1}$; NMR (DMSO) d: 2.03 (m, 1H), 2.27 (m, 1H), 2.32 (s, 3H), 3.50 (m, 1H), 3.59 (m,1H), 3.75 (m, 2H), 3.88 (m, 2H), 3.95 (m, 1H), 7.08 (m, 2H), 7.52 (m, 1H), 7.92 (m, 1H),. 8.24 (m, 1H), 9.10 (m, 1H). Analysis calculated with 1/3 mol of $H_2O$ for C, 57.60; H, 4.49; N, 9.60. Found: C, 57.82; H, 4.45; N, 9.44.

EXAMPLE 7

1-(3-aminopyrrolidin-1-yl)-2,9-difluoro-4-oxo-4H-quino[2,3,4-i,j][1,4]benzoxazine-5-carboxylic acid hydrochloride Step 1: Ethyl 1,2,9-trifluoro-4-oxo-4H-quino[2,3,4-i,j][1,4]benzoxazine-5-carboxylate Ethyl-3-(2'-hydroxy, 4'-fluoroanilino)-2-(2,3,4,5-tetrafluorobenzoyl)acrylate was prepared by a method similar to that described in the *J. Heterocycl. Chem.*, 24:453 (1987) from ethyl 2,3,4,5-tetrafluorbenzoylacetate. m.p. 205° C.; MS M/Z: 402 (M+H); IR(KBr) 1630, 1670 $cm^{-1}$; NMR (DMSO-d6) d: 1.05 (m, 3H), 4.03 (m 2H), 6.75 (m, 2H), 7.50 (m, 1H), 7.65 (m, 1H), 8.54 (m, ½H), 8.68 (m, 1H), 11.25 (m, ½H), 12.64(m, 1H)). Analysis calculated for C, 53.87; H, 3.01; N, 3.49. Found C, 53.65 H, 3.08; N, 3.43.

The product of the above reaction was then cyclized in the presence of sodium bicarbonate and dimethylformamide (DMF) as described in Scheme 1 to yield ethyl 1,2,9-trifluoro-4-oxo-4H-quino[2,3,4-i,j][1,4]benzoxazine-5-carboxylate. m.p. 237°–8° C.; MS M/Z: 362 (M+H); IR (KBr) 1690, 1730 $cm^{-1}$; NMR (DMSO) d: 1.32 (m, 3H), 4.28 (m, 2H), 7.15 (m, 1H), 7.39 (m, 1H), 7.63 (m, 1H), 8.05 (m, 1H), 9.03 (s, 1H). Analysis calculated for C, 59.84; H, 2.79; N, 3.88. Found: C, 59.65; H, 2.86; N, 3.89.

Step 2: Ethyl 1-(3-acetamidopyrrolidin-1-yl)-2,9-difluoro-4-oxo-4H-quino[2,3,4-i,j][1,4]benzoxazine-5-carboxylate Ethyl 1,2,9-trifluoro-4-oxo-4H-quino[2,3,4-i,j][1,4]benzoxazine-5-carboxylate was then reacted as described in U.S. Pat. No. 4,607,032 to yield ethyl 1-(3-acetamidopyrrolidin-1-yl)-2,9 difluoro-4-oxo-4H-quino[2,3,4-i,j][1,4]benzoxazine-5-carboxylate. m.p. 248°–51° C.; MS M/Z: 470 (M+H); IR (KBr) 1660, 1695, 1720 $cm^{-1}$; NMR (DMSO) d: 1.30 (m, 3H), 1.85 (m, 4H), 2.10 (m, 1H), 3.42 (m, 2H), 3.72 (m, 2H), 3.86 (m, 1H), 4.25 (m, 2H), 7.06 (m, 1H), 7.25 (m, 1H), 7.35(m, 1H), 7.86 (m, 1H), 8.15 (m, 1H), 8.83 (s, 1H). Analysis calculated with ½ mol of $H_2O$ for C, 60.24; H, 4.63; N, 8.78. Found: C, 60.40; H, 4.53; N, 8.79.

Step 3: 1-(3-aminopyrrolidin-1-yl)-2,9-difluoro-4-oxo-4H-quino[2,3,4i,j][1,4]benzoxazine-5-carboxylic acid hydrochloride Ethyl 1-(3-acetamidopyrrolidin-1-yl)-2,9-difluoro-4-oxo-4H-quino[2,3,4-i,j][1,4]benzoxazine-5-carboxylate was then deprotected by a method similar to that described in the *J. Heterocycl. Chem.*, 24:453 (1987) to yield 1-(3-aminopyrrolidin-1-yl)-2,9-difluoro-4-oxo-4H-quino[2,3,4-i,j][1,4]benzoxazine-5-carboxylic acid hydrochloride. m.p. 285° C. (dec); MS M/Z: 400 (M+H); IR (KBr) 1625, 1720 $cm^{-1}$; NMR (DMSO) d: 1.85 (m, 1H), 2.03 (m, 1H), 2.27 (m, 1H), 3.50 (m, 1H), 3.61 (m, 1H), 3.85 (m, 3H), 7.10 (m, 2H), 7.25 (m, 1H), 7.39 (m, 1H), 7.50 (m, 1H), 8.10 (m, 2H), 8.37 (m, 2H), 9.08 (m, 1H). Analysis calculated for $C_{20}H_{16}ClFN_3O_4 \cdot ½ H_2O$: C, 54.00; H, 3.85; N, 9.45. Found: C, 54.02; H, 3.63; N, 9.23.

EXAMPLE 8

1-(3-norvalylaminopyrrolidin-1-yl)-2-fluoro-4-oxo-4H-quino[2,3,4-i,j][1,4]benzoxazine-5-carboxylic acid hydrochloride Step 1: 1-(t-N-butyloxycarbonyl-norvalylaminopyrrolidin-1-yl)-2-fluoro-4-oxo-4H-quino[2,3,4-i,j][1,4]benzoxazine-8-carboxylic acid 1-(3-Aminopyrrolidin-1-yl)-2-fluoro-4-oxo-4H-quino[2,3,4-i,j][1,4]benzoxazine-5-carboxylic acid hydrochloride (4.27 g, 0.102 mmol), prepared as described in *J. Heterocyclic Chem.* 24:453–456 (1987), was suspended in dry N,N-dimethyl formamide (DMF) (100 mL) and N-methylmorpholine (2.17 g, 0.0215M) was added and the suspension stirred overnight.

After overnight stirring, the solution was cooled in an ice-bath for 15 minutes, then t-butyloxycarbonyl-L-norvaline-N-hydroxyphthalimide (3.36 g, 0.0107M) was added in one portion. The resulting solution was cooled in an ice-bath for an additional hour, following by stirring at room temperature for several days. After the third day, an additional 730 mg of N-carbobenzyloxy-L-norvaline-N-hydroxyphthalimide was added and the reaction allowed to proceed overnight with stirring. An additional 1.29 g of the hydroxyphthalimide ester was added and the reaction stirred at room temperature for an additional day.

The resulting solution was poured into 500 mL of 0.5N aqueous hydrochloric acid solution and the mixture extracted with 2×250 mL portions of chloroform. The combined extracts were washed with 5% aqueous sodium bicarbonate solution and the organic phase dried over anhydrous magnesium sulfate and evaporated to leave a solution of DMF and product. The residual DMF was removed by co-distillation with toluene and ethylene dichloride to leave a yellow colored solid. Diethyl ether was added to the solid and the suspension was stirred overnight at room temperature. The suspension was separated by filtration and the solid washed with fresh ether and dried overnight under vacuum at 55° C. to yield 3.332 g (0.0057M, 56% yield) g of 1-(t-N-butyloxycarbonyl-norvalylaminopyrrolidin-1-yl)-2-fluoro-4-oxo-4H-quino[2,3,4-i,j][1,4]benzoxazine-5-carboxylic acid; mp.209° C.; MS M/Z: 581 (M+H). NMR (DMSO-d6) d: 0.84 (m, 3H), 1.45 (m, 13H), 1.88 (m, 1H), 2.10 (m ,1H), 3.21 (m: 2H), 3.74 (m, 1H), 3.89 (m, 2H), 4.31 (m, 1H), 6.78 (m, 1H), 7.23 (m, 2H), 7.36 (m, 1H), 7.48 (d, 1H), 8.01 (m, 1H), 8.12 (m, 1H), 9.08 (s, 1H).

Step 2: 1-(3-norvalylaminopyrrolidin-1-yl)-2-fluoro-4-oxo-4H-quino[2,3,4-i,j][1,4]benzoxazine-5-carboxylic acid hydrochloride 1-(t-N-butyloxycarbonyl-norvalylaminopyrrolidin-1-yl)-2-fluoro-4-oxo-4-4H-quino[2,3,4,-i,j][1,4]benzoxazine-5-carboxylic acid (3.26 g, 0.00561 mM) was added to 100 mL of 1M hydrochloric acid in acetic acid and the suspension stirred at room temperature for 1.5 hours. The suspension was then diluted with with acetic acid and the solution evaporated under reduced pressure. The resulting residue was co-distilled with ethanol and methanol and added under vacuum overnight. Ether was added to the residue and the mixture allowed to stand for several hours. The solid was collected by filtration and washed with fresh ether and dried to yield 2.59 g (0.0054 mM, 96% yield) of the desired product; mp=178°–180°, MS M/Z: 481 (M+H).$^{NMR}$ (CD$_3$OD) d: 0.99 (m, 3H), 1.46 (m, 2H), 1.85 (m, 2H), 2.06 (m,1H), 2.25 (m, 1H), 3.66 (m, 1H), 3.77 (m, 1H), 3.80 (m, 1H), 4.07 (m, 2H), 4.48 (m, 1H) 7.26 (m, 4H), 7.63 (m, 1H), 9.82 (m, 1H).

EXAMPLE 9

1-(3-alanylaminopyrrolidin-1-yl)-2-fluoro-9-methyl-4-oxo-4H-quino[2,3,4-i,j][1,4]benzoxazine-5-carboxylic acid hydrochloride Step 1: 1-(t-N-butyloxycarbonylate-alanylaminopyrrolidin-1-yl)-2-fluoro-9-methyl-4-oxo-4H-quino[2,3,4-i,j][1,4]benzoxazine-5-carboxylic acid 1-(t-N-butyloxycarbonyl-alanylaminopyrrolidin-1-yl)-2-fluoro-9-methyl-4-oxo-4H-quino[2,3,4i,j][1,4]benzoxazine-5-carboxylic acid was prepared from 1-(3-aminopyrrolidin-1-yl)-2-fluoro-9-methyl-4-oxo-4H-quino[2,3,4-i,j][1,4]benzoxazine-5-carboxylic acid hydrochloride as described in Example 8. m.p. 213° C. (dec); MS M/Z: 567 (M+H); IR (KBr) 1633, 1675, 1710 cm$^{-1}$; NMR (DMSO-d6) d: 1.17 (m, 3H), 1.35 (m, 9H), 1.98 (m, 1H), 2.10 (m, 1H), 2.31 (s, 3H), 3.48 (m, 1H), 3.75 (m, 1H), 3.85 (m, 1H), 3.95 (m, 2H), 4.30 (m, 1H), 6.82 (m, 1H), 7.05 (m, 2H), 7.45 (d, 1H), 7.85 (d, 1H), 8.06 (m, 1H), 9.03 (s, 1H), 14.96 (s, 1H). Analysis calculated for C$_{29}$H$_{31}$FN$_4$O$_7$: C, 61.47; H, 5.52; N, 9.89. Found: C, 61.25; H, 5.54; N, 9.78.

Step 2: 1-(3-alanylaminopyrrolidin-1-yl)-2-fluoro-9-methyl-4-oxo-4H-quino[2,3,4-i,j][1,4]benzoxazine-5-carboxylic acid hydrochloride.

1-(t-N-butyloxycarbonyl-alanylaminopyrrolidin-1-yl)-2-fluoro-9-methyl-4-oxo-4H-quino[2,3,4-i,j][1,4]benzoxazine-5-carboxylic acid was deprotected as described in Example 8. to give the title compound. NMR (DMSO) d: 1.35 (m, 3H), 1.90 (m, 1H), 2.16 (m, 1H), 2.31 (s, 3H), 3.51 (m, 1H), 3.82 (m, 3H), 4.11 (m, 1H), 4.46 (m, 1H), 7.03 (m, 1H), 7.12 (m, 1H), 7.48 (m, 1H), 7.85 (m, 1H), 8.82 (m, 1H), 9.02 (m, 1H).

EXAMPLE 10

1-(3-norvalylaminopyrrolidin-1-yl)-2-fluoro-9-methyl-4-oxo-4H-quino[2,3,4-i,j][1,4]benzoxazine-5-carboxylic acid hydrochloride Step 1: 1-(t-N-butyloxycarbonyl-norvalylaminopyrrolidin-1-yl)-2-fluoro-9-methyl-4-oxo-4H-quino[2,3,4-i,j][1,4]benzoxazine-5-carboxylic acid 1-(t-N-butyloxycarbonyl-norvalylaminopyrrolidin-1-yl)-2-fluoro-9-methyl-4-oxo-4H-quino[2,3,4-i,j][1,4]benzoxazine-5-carboxylic acid was prepared from 1-(3-aminopyrrolidin-1-yl)-2-fluoro-9methyl-4-oxo-4H-quino[2,3,4-i,j][1,4]benzoxazine-5-carboxylic acid hydrochloride as described in Example 8. mp. 182°–5° C.; MS M/Z: 595 (M+H); IR (KBr) 1630, 1670, 1715 cm$^{-1}$; NMR (CDCl$_3$) d: 0.95 (m, 3H), 1.41 (m, 9H), 1.54 (m, 2H), 1.83 (m, 2H), 2.12 (m, 2H), 2.46 (s, 3H), 3.66 (m, 2H), 4.03 (m, 2H), 4.13 (m, 1H), 4.60 (m, 1H), 5.10 (m, 1H), 6.94 (m, 3H), 7.41 (m, 2H), 8.80 (m, 1H), 14.91 (s, 1H). Analysis calculated with 1/2 mole of H$_2$O for C, 61.68; H, 6.01; N, 9.28. Found C, 61.80; H, 5.96, N, 9.29.

Step 2: 1-(3-norvalylaminopyrrolidin-1-yl)-2-fluoro-9-methyl-4-oxo-4H-quino[2,3,4i,j][1,4]benzoxazine-5-carboxylic acid hydrochloride.

1-(t-N-butyloxycarbonyl-norvalylaminopyrrolidin-1-yl)-2-fluoro-9-methyl-4-oxo-4H-quino[2,3,4,-i,j][1,4]benzoxazine-5-carboxylic acid (3.26 g, 0.00561 mM) was deprotected as described in Example 8 to yield the title compound; mp=190°–2°, MS M/Z: 495 (M+H); IR (KBr) 1630, 1680, 1720 cm$^{-1}$; NMR (DMSO) d: 1.01 (m, 3H), 1.47 (m, 2H), 1.86 (m, 2H), 2.02 (m, 1H), 2.17 (m, 1H), 2.33 (s, 3H), 3.63 (m, 1H), 3.74 (m, 1H), 3.91 (m, 2H), 4.03 (m, 1H), 4.48 (m, 1H), 6.97 (m, 3H), 7.33 (m, 1H), 7.48 (m, 1H), 8.83 (m, 1H).

EXAMPLE 11

1-(3-norvalylaminopyrrolidin-1-yl)-2-fluoro-8-methyl-4-oxo-4H-quino[2,3,4-i,j][1,4]benzoxazine-5-carboxylic acid hydrochloride Using methods as described in Example 8 step 1, 1-(3-aminopyrrolidin-1-yl)-2-fluoro-8-methyl-4-oxo-4H-quino [2,3,4-i,j][1,4]benzoxazine-5-carboxylic acid hydrochloride was converted to 1-(3-N-t-butoxycarbonylnorvalylaminopyrrolidin-1-yl)-2-fluoro-8-methyl-4-oxo-4H-quino[2,3,4-i,j][1,4]benzoxazine-5-carboxylic acid, mp 225° C. (dec). MS M/Z 595 (M+H). IR (KBr) 1630, 1720 cm$^{-1}$. NMR (DMSO) δ: 0.83 (m, 3H), 1.25 (m, 2H), 1.36 (m, 9H), 1.50 (m, 2H), 1.85 (m, 2H), 2.11 (m, 2H), 2.36 (m, 3H), 3.50 (m, 2H), 3.75 (m, 1H), 3.90 (m, 2H), 4.30 (m, 1H), 6.75 (m, 1H), 7.16 (m, 1H), 7.48 (m, 1H), 7.88 (m, 1H), 8.10 (m, 1H), 9.13 (m, 1H), 14.95 (m, 1H). Analysis calculated for C31H$_{35}$FN$_4$O$_7$: C, 62.61; H, 5.93; N, 9.42. Found: C, 62.35; H, 5.67; N, 8.99.

Following the procedure of Example 8 step 2, the boc-protecting group was removed to afford 1-(3-norvalylaminopyrrolidin-1-yl)-2-fluoro-8-methyl-4-oxo-4H-quino[2,3,4-i,j][1,4]benzoxazine-5-carboxylic acid hydrochloride, mp 246°–9° C. MS M/Z 495 (M+H). IR (KBr): 1640, 1680, 1720 cm$^{-1}$. NMR (DMSO) δ: 0.85 (m, 3H), 1.30 (m, 2H), 1.68 (m, 2H), 1.91 (m, 2H), 2.16 (m, 2H), 2.34 (m, 3H), 3.53 (m, 1H), 3.73 (m, 2H), 3.92 (m, 2H), 7.15 (m, 2H), 7.45 (m, 1H), 7.86 (m, 1H), 8.92 (m, 2H), 9.08 (m, 1H).

EXAMPLE 12

Using the methods described in Examples 6, 8, and 9 and in U.S. Pat. Nos. 4,528,285 and 4,529,725, or in Scheme II, the following compounds can be prepared by substitution of 2-thioaniline, substituted 2-thioanilines, or thioprotected 2-thioanilines in place of 2-hydroxyanilines:

(a) 1-(3-aminopyrrolidin-1-yl)-2-fluoro-4-oxo-4H-quino [2,3,4-i,j][1,4]benzothiazine-5-carboxylic acid;

(b) 1-(3-norvalylaminopyrrolidin-1-yl)-2-fluoro-4-oxo-4H-quino[2,3,4-i,j][1,4]benzothiazine-5-carboxylic acid;

(c) 1-(3-alanylaminopyrrolidin-1-yl)-2-fluoro-4-oxo-4H-quino[2,3,4-i,j][1,4]benzothiazine-5-carboxylic acid;

(d) 1-(3-aminopyrrolidin-1-yl)-2-fluoro-9-methyl-4-oxo-4H-quino[2,3,4-i,j][1,4]benzothiazine-5-carboxylic acid;

(e) 1-(3-norvalylaminopyrrolidin-1-yl)-2-fluoro-9-methyl-4-oxo-4H-quino[2,3,4i,j][1,4]benzothiazine-5-carboxylic acid;

(f) 1-(3-alanylaminopyrrolidin-1-yl)-2-fluoro-9-methyl-4-oxo-4H-quino[2,3,4-i,j][1,4]benzothiazine-5-carboxylic acid;

(g) 1-(3-aminopyrrolidin-1-yl)-2-fluoro-8-methyl-4-oxo-4H-quino[2,3,4-i,j][1,4]benzothiazine-5-carboxylic acid;

(h) 1-(3-norvalylaminopyrrolidin-1-yl)-2-fluoro-8-methyl-4-oxo-4H-quino[2,3,4-i,j][1,4]benzothiazine-5-carboxylic acid; and (i) 1-(3-alanylaminopyrrolidin-1-yl)-2-fluoro-8-methyl-4-oxo-4H-quino[2,3,4-i,j][1,4]benzothiazine-5-carboxylic acid

EXAMPLE 13

Using the method described in Scheme III, the compound 1H,7H-pyrido[3,2,1-de]acridine-3-one-5-fluoro-6-(3-aminopyrrolidin-1-yl)-2-carboxylic acid can be prepared.

EXAMPLE 14

Using the method described in Scheme I, ethyl 4-oxo-1,2,8,9,10-pentafluoro-4H-quino[2,3,4-i,j][1,4]benzoxazine-5-carboxylate can be prepared from 2-hydroxy-3,4,5-trifluoroaniline.

EXAMPLE 15

1-(3-aminopyrrolidin-1-yl)-8,10-dimethyl-2-fluoro-4-oxo-4H-quino[2,3,4-i,j][1,4]benzoxazine-5-carboxylic acid hydrochloride Step 1. Ethyl 3-(2-hydroxy-3,5-dimethylanilino)-2-(2,3,4,5-tetrafluorobenzoyl)acrylate A solution of 15.52 g (0.058 mol) of ethyl 2,3,4,5-tetrafluorobenzoylacetate (from Example 1 step 2) in 14.6 mL (0.088 mol) of triethylorthoformate and 25 mL of acetic anhydride (0.263 mol) was heated at 130° C. for 4 hours. The solution was diluted with toluene and the solvent was removed by evaporation to leave an oily residue. The oil was azeotroped with toluene several times to remove any remaining volatile starting materials. The residue was dissolved in 200 mL of acetonitrile and 8.06 g (0.0588 mol) of 6-amino-2,4-dimethylphenol was added with stirring. A solid immediately precipitated, and the mixture was allowed to stir at room temperature for 20 hours. The solvent was removed by evaporation under vacuum, and the solid residue was triturated in toluene, which was filtered and removed to afford 18.24 g of the title compound, mp 199° C. (dec). MS M/Z: 412 (M+H). IR (KBr): 1630, 1670 cm$^{-1}$. NMR (CDCl$_3$) δ: 1.10 m, 3H), 2.30 (m, 6H), 4.13 (m, 4H), 6.80 (m, 1H), 7.05 (m, 1H), 7.15 (m, 1H), 8.60 (m, 1H). Analysis calculated for C$_{20}$H$_{17}$F$_4$NO$_4$: C, 58.39; H, 4.16; N, 3.40. Found: C, 57.94; H, 4.01; N, 3.40.

Step 2. Ethyl 1,2-difluoro-8,10 dimethyl-4-oxo-4H-quino[2,3,4-i,j][1,4]benzoxazine-5-carboxylate The compound from step 1 above (18.2 g, 0.044 mol) was dissolved in 200 mL of DMF and 11.2 g (0.133 mol) of sodium bicarbonate was added. This mixture was stirred with heating at 100° C. for 2 hours. After cooling, the solvent was removed under reduced pressure. The solid was washed with water, collected by filtration, and dissolved in chloroform, and this solution was washed with 0.5N HCl and 5% potassium carbonate solutions. The solvent was dried and removed under vacuum. The residue was triturated in ether, the solid was filtered and dried to afford 14.47 g of the title compound as an orange solid, mp 221°–2° C. MS M/Z: 372 (M+H). IR (CDCl$_3$): 1630, 1690 cm$^{-1}$. NMR (CDCl$_3$) δ: 1.45 (m, 3H), 2.26 (m, 6H), 4.45 (m, 2H), 6.94 (m, 1H), 7.13 (m, 1H), 7.78 (m, 1H), 8.96 (s, 1H). Analysis calculated for C$_{20}$H$_{15}$F$_2$NO$_4$·¼ H$_2$O: C, 63.91; H, 4.15; N, 3.73. Found: C, 64.04; H, 3.84; N, 3.83.

Step 3. 1,2-difluoro-8,10 dimethyl-4-oxo-4H-quino[2,3,4-i,j][1,4]benzoxazine-5-carboxylic acid A suspension of 5.66 g (0.015 mmol) of the compound from Step 2 in 500 mL of 1N HCl and 50 mL of ethanol was heated at 90° C. for 72 hours. After cooling, to room temperature, the solid was filtered off and dried to afford 5.06 g of the title compound, mp>270° C. IR (KBr): 1630, 1720 cm$^{-1}$. NMR (TFA) δ: 2.53 (m, 6H), 7.42 (m, 1H), 7.70 (m, 1H), 8.06 (m, 1H), 9.73 (m, 1H). Analysis calculated for C$_{18}$H$_{11}$F$_2$NO$_4$: C, 62.97; H, 3.23; N, 4.08. Found: C, 63.30; H, 3.43; N, 4.04.

Step 4. 1-(3-(N-t-butoxycarbonylamino)pyrrolidin-1-yl)-8,10 dimethyl-2-fluoro-4-oxo-4H-quino[2,3,4-i,j][1,4]benzoxazine-5-carboxylic acid A 2.85 g (8.30 mmol) of the compound from Step 3 was dissolved in 70 mL of pyridine and 2.6 mL (0.018 mol) of triethylamine and 3.40 g (0.018 mol) of 3-(t-butoxycarbonylamino)pyrrolidine were added. The solution was heated at 85° C. for 96 hours. The solvent was removed under vacuum, the residue dissolved in chloroform and the solvent washed with 10% citric acid solution. After drying, the solvent was removed to afford 3.59 g of the title compound as a light yellow solid, mp 226° C. (dec). MS M/Z: 510 (M+H). IR (KBr): 1630, 1720 cm$^{-1}$. NMR (DMSO) d: 1.40 (m, 9H), 1.85 (m, 2H), 2.05 (m, 2H), 2.25 (m, 6H), 3.50 (m, 1H), 3.75 (m, 1H), 3.88 (m, 1H), 4.05 (m, 2H), 7.00 (m, 1H), 7.40 (m, 1H), 7.58 (m, 1H), 8.95 (m, 1H), 14.90 (m, 1H). Analysis calculated for C$_{27}$H$_{28}$FN$_3$O$_6$: C, 63.64; H, 5.54; N, 8.25. Found: C, 63.31; H, 5.40; N, 7.72.

Step 5. 1-(3-aminopyrrolidin-1-yl)-8,10-dimethyl-2-fluoro-4-oxo-4H-quino[2,3,4-i,j][1,4]benzoxazine-5-carboxylic acid hydrochloride A suspension of 3.57 g (7.01 mmol) of the compound from Step 4 in 150 mL of 1M HCl in acetic acid was stirred at room temperature for 1.5 hours. The solvent was removed under vacuum and the solid was suspended in alcohol. The solvents were removed to afford the 2.47 g of the title compound as a yellow solid, mp 255°–257° C. MS M/Z 410 (M+H). IR (KBr) 1720, 1630 cm$^{-1}$. NMR (TFA) d: 2.46 (m, 6H), 2.63 (m, 4H), 4.13 (m, 1H), 4.39 (m, 1H), 4.55 (m, 3H), 7.32 (m, 1H), 7.52 (m, 1H), 7.91 (m, 1H), 9.48 (m, 1H). Analysis calculated for C$_{22}$H$_{21}$ClFN$_3$O$_4$: C, 59.26; H, 4.75; N, 9.43. Found: C, 59.63; H, 4.70; N, 8.77.

EXAMPLE 16

1((3S)-3-aminopyrrolidin-1-yl)-2-fluoro-4-oxo-4H-quino[2,3,4-i,j][1,4]benzoxazine-5-carboxylic acid hydrochloride Step 1. Ethyl1-((3S)-3-(N-t-butoxycarbonylamino)pyrrolidin-1-yl)-2-fluoro-4-oxo-4H-quino[2,3,4-i,j][1,4]benzoxazine-5-carboxylate The procedure of Example 15 step 4 was followed, and 3-(N-t-butoxycarbonylamino)pyrrolidine was replaced with (3S)-3-(N-t-butoxycarbonylamino)pyrrolidine (obtained from American Tokyo Kasei, Div. of Tokyo Kasei Kogyo, K.K.) to afford the title compound, mp 135°–7° C. MS M/Z: 510 (M+H). IR (CDCl$_3$): 1620, 1690, 1720 cm$^{-1}$. NMR (CDCl$_3$) δ: 1.45 (m, 12H), 1.92 (m, 2H), 2.22 (m, 2H), 3.50 (m, 1H), 3.65 (m, 1H), 3.82 (m, 1H), 3.92 (m, 1H), 4.42 (m, 2H), 7.08 (m, 1H), 7.20 (m, 2H), 7.42 (m, 1H), 7.62 (m, 1H), 8.86 (s, 1H). Analysis calculated for C$_{27}$H$_{28}$FN$_3$O$_6$·⅓ H$_2$O: C, 62.90; H, 5.60; N, 8.15. Found: C, 62.99; H, 5.42; N, 8.32.

Step 2. 1-((3S)-3-aminopyrrolidin-1-yl)-2-fluoro-4-oxo-4H-quino[2,3,4-i,j][1,4]benzoxazine-5-carboxylic acid hydrochloride A suspension of the compound from Step 1 was deprotected as in Example 18 step 2 to afford the title compound, mp>285° C. MS M/Z: 382 (M+H). IR (KBr): 1630, 1720 cm$^{-1}$. NMR (DMSO) δ: 2.03 (m, 2H), 2.26 (m, 2H), 3.78 (m, 2H), 3.88 (m, 2H), 3.95 (m, 1H), 7.35 (m, 3H), 7.52 (m, 1H), 8.04 (m, 1H), 9.13 (s, 1H). Analysis calculated for $C_{20}H_{17}ClF_3O_4$: C, 57.49; H, 4.10; N, 10.06. Found: C, 57.32; H, 4.11; N, 10.00.

EXAMPLE 17

1-((3R)-3-aminopyrroidin-1-yl)-2-fluoro-4-oxo-4H-quino[2,3,4-i,j][1,4]benzoxazine-5-carboxylic acid hydrochloride Step 1. Ethyl 1-((3R)-3-(N-t-butoxycarbonylamino)pyrrolidin-1-yl)-2-fluoro-4-oxo-4H-quino[2,3,4-i,j][1,4]benzoxazine-5-carboxylacte The procedure of Example 15 Step 4 was followed, and 3-(N-t-butoxycarbonylamino)pyrrolidine was replaced with (3R)-3-(N-t-butoxycarbonylamino)pyrrolidine (obtained from American Tokyo Kasei, Div. of Tokyo Kasei Kogyo, K.K.) to afford the title compound, mp 135°–7° C. MS M/Z: 510 (M+H). IR (CDCl$_3$): 1620, 1690, 1720 cm$^{-1}$. NMR (CDCl$_3$) δ: 1.43 (m, 12H), 1.91 (m, 2H), 2.23 (m, 2H), 3.50 (m, 1H), 3.65 (m, 1H), 3.82 (m, 1H), 3.92 (m, 1H), 4.42 (m; 2H), 7.08 (m, 1H), 7.19 (m, 2H), 7.41 (m, 1H), 7.62 (m, 1H), 8.86 (s, 1H). Analysis calculated for $C_{27}H_{28}FN_3O_6 \cdot 1/3 H_2O$: C, 62.90; H, 5.60; N, 8.15. Found: C, 62.83; H, 5.35; N, 8.26.

Step 2. 1-((3R)-3-aminopyrrolidin-1-yl)-2-fluoro-4-oxo-4H-quino[2,3,4-i,j][1,4]benzoxazine-5-carboxylic acid hydrochloride.

A suspension of the compound from Step 1 was deprotected as in Example 18 step 2 to afford the title compound, mp>285° C. MS M/Z: 382 (M+H). IR (KBr): 1630, 1720 cm$^{-1}$. NMR (DMSO) δ: 2.03 (m, 2H), 2.26(m, 2H), 3.78 (m, 2H), 3.88 (m, 2H), 3.95 (m, 1H), 7.35 (m, 3H), 7.55 (m, 1H), 8.04 (m, 1H), 9.13 (s, 1H). Analysis calculated for $C_{20}H_{17}ClFN_3O_4 \cdot 3/4 H_2O$: C, 55.68; H, 4.32; N, 9.74. Found: C, 55.67; H, 4.00; N, 9.67.

EXAMPLE 18

1-((3S)-3-aminopyrrolidin-1-yl)-2-fluoro-9-methyl-4-oxo-4H-quino[2,3,4-i,j][1,4]benzoxazine-5-carboxylic acid hydrochloride Step 1: Ethyl 1-((3S)-3-N-t-butoxycarbonylaminopyrrolidin-1-yl)-2-fluoro-9-methyl-4-oxo-4H-quino[2,3,4-i,j][1,4]benzoxazine-5-carboxylate.

Following the procedure described in U.S. Pat. No. 4,607,032, ethyl 1,2-difluoro-9-methyl-4-oxo-4H-quino[2,3,4-i,j][1,4]benzoxazine-5-carboxylate (from Example 6 Step 1) was reacted with (3S)-3-(N-t-butoxycarbonylamino)pyrrolidine (obtained from American Tokyo Kasei, Div. of Tokyo Kasei Kogyo, K.K.) to afford the title compound, mp 187°–190° C. MS M/Z: 524 (M+H). IR (CDCl$_3$): 1630, 1690, 1710 cm$^{-1}$. NMR (CDCl$_3$) δ: 1.45 (m, 12H), 1.91 (m, 2H), 2.23 (m, 2H), 2.45 (s, 3H), 3.50 (m, 1H), 3.63 (m, 1H), 3.82 (m, 1H), 3.93 (m, 1H), 4.42 (m, 2H), 6.90 (m, 1H), 6.95 (m, 1H), 7.30 (m, 1H), 7.63 (m, 1H), 8.84 (s, 1H). Analysis calculated for $C_{28}H_{30}FN_3O_6 \cdot 1/2 H_2O$: C, 63.14; H, 5.87; N, 7.89. Found: C, 62.90; H, 5.48; N, 7.92.

Step 2: 1-((3S)-3-aminopyrrolidin-1-yl)-2-fluoro-9-methyl-4-oxo-4H-quino[2,3,4-i,j][1,4]benzoxazine-5-carboxylic acid hydrochloride A suspension of 4.50 g of the compound from Step 1 in 450 mL of 1M HCl and 45 mL of ethanol was stirred at 90° C. for 64 hours. The reaction was cooled at refrigerator temperature (5° C.) for 4 hours The product was removed by filtration, washed with water and methanol, and dried to afford 3.5 g of the title compound as a yellow solid, mp>285° C. MS M/Z: 396 (M+H). IR (KBr): 1620, 1720 cm$^{-1}$. NMR (DMSO) δ: 202 (m, 2H), 2.30 (m, 5H), 3.76 (m, 2H), 3.88 (m, 2H), 3.95 (m, 1H), 7.08 (m, 1H), 7.17 (m, 1H), 7.53 (m, 1H), 7.92 (m, 1H), 9.11 (s, 1H). Analysis calculated for $C_{20}H_{19}ClFN_3O_4 \cdot 1/2 H_2O$: C, 57.20; H, 4.50; N, 9.53. Found: C, 57.47; H, 4.32; N, 9.40.

EXAMPLE 19

1-((3R)-3-aminopyrrolidin-1-yl)-2-fluoro-9-methyl-4-oxo-4H-quino[2,3,4-i,j][1,4]benzoxazine-5-carboxylic acid hydrochloride Step 1: Ethyl 1-((3R)-3-(N-t-butoxycarbonylaminopyrrolidin-1-yl)-2-fluoro-9-methyl-4-oxo-4H-quino[2,3,4-i,j][1,4]benzoxazine-5-carboxylate.

Following the procedure described in U.S. Pat. No. 4,607,032, ethyl 1,2-difluoro-9-methyl-4-oxo-4H-quino[2,3,4-i,j][1,4]benzoxazine-5-carboxylate (from Example 6 Step 1) was reacted with (3R)-3-(N-t-butoxycarbonylamino)pyrrolidine (obtained from American Tokyo Kasei, Div. of Tokyo Kasei Kogyo, K.K.) to afford the title compound, mp 194°–5° C. MS M/Z: 524 (M+H). IR (CDCl$_3$): 1630, 1690, 1720 cm$^{-1}$. NMR (CDCl$_3$) δ: 1.45 (m, 12H), 1.91 (m, 2H), 2.23 (m, 2H), 2.35 (s, 3H), 3.50 (m, 1H), 3.64 (m, 1H), 3.82 (m, 1H), 3.92 (m, 1H), 4.42 (m, 2H), 6.89 (m 1H), 6.95 (m, 1H), 7.30 (m, 1H), 7.62 (m, 1H), 8.83 (s, 1H). Analysis calculated for $C_{28}H_{30}FN_3O_6 \cdot 3/4 H_2O$: C, 62.62; H, 5.91; N, 7.83. Found: C, 62.46; H, 5.92; N, 7.73.

Step 2: 1-((3R)-3-aminopyrrolidin-1-yl)-2-fluoro-9-methyl-4-oxo-4H-quino[2,3,4-i,j][1,4]benzoxazine-5-carboxylic acid hydrochloride Following the procedure of Example 18, step 2, the protecting group and ester group were removed from the compound from step 1 above, to afford the title compound, mp>280° C. MS M/Z 396 (M+H). IR (KBr) 1620, 1710 cm$^{-1}$. NMR (TFA) d: 2.51 (m, 3H), 2.68 (m, 2H), 4.13 (m, 1H), 4.54 (m, 4H), 7.23 (m, 1H), 7a.30 (m, 1H), 7.78 (m, 1H), 7.94 (m, 1H), 9.50 (m, 1H). Analysis calculated for $C_{21}H_{18}FN_3O_4$: C, 58.54; H, 4.21; N, 9.75. Found: C, 58.11; H, 4.50; N, 9.62.

EXAMPLE 20

2-fluoro-1-(3-alanylaminopyrrolidin-1-yl)-8-methyl-4-oxo-4H-quino[2,3,4-i,j][1,4]benzoxazine-5-carboxylic acid hydrochloride Using methods as described in Example 9 step 1, 1-(3-aminopyrrolidin-1-yl)-2-fluoro-8-methyl-4-oxo-4H-quino[2,3,4-i,j][1,4]benzoxazine-5-carboxylic acid hydrochloride was converted to 1-(3-N-t-butoxycarbonylalanylaminopyrrolidin-1-yl)-2-fluoro-8-methyl-4-oxo-4H-quino[2,3,4-i,j][1,4]benzoxazine-5-carboxylic acid, mp 217 (dec). MS M/Z 567 (M+H). IR (CDCl$_3$): 1630, 1670, 1710 cm$^{-1}$. NMR (DMSO) δ: 1.40 (m, 3H), 1.42 (m, 9H), 2.05 (m, 2H), 2.20 (m, 2H), 2.38 (m, 3H), 3.64 (m, 2H), 4.03 (m, 2H), 4.20 (m, 1H), 5.02 (m, 1H), 7.03 (m, 2H), 7.23 (m, 2H), 7.50 (m, 1H), 8.86 (m, 1H), 14.86 (m, 1H).

Following the procedure of Example 8 step 2, the boc-protecting group was removed to afford 1-(3-alanylaminopyrrolidin-1-yl)-2-fluoro-8-methyl-4-oxo-4H-quino[2,3,4-i,j][1,4]benzoxazine-5-carboxylic acid hydrochloride, mp 210°–212° C. MS M/Z 467 (M+H). IR (KBr): 1630, 1680, 1720 cm$^{-1}$. NMR (DMSO) δ: 1.36 (m, 3H), 1.90 (m, 2H), 2.18 (m, 2H), 2.34 (m, 3H), 3.53 (m, 1H), 3.75 (m, 2H), 3.84 (m, 2H), 3.96 (m, 1H), 4.34 (m, 1H), 7.13 (m, 2H), 7.42 (m, 1H), 7.83 (m, 1H), 8.86 (m, 1H), 9.05 (m, 1H).

EXAMPLE 21

1-(3-aminopyrrolidin-1-yl)-8-t-butyl-2-flouro-4-oxo-4H-quino[2,3,4-i,j][1,4]benzoxazine-5-carboxylic acid hydrochloride Step 1. Ethyl 3-(5-t-butyl-2-hydroxyanilino)-2-(2,3,4,5-tetrafluorobenzoyl)acrylate Following the procedure of Example 15 step 1 and replacing 6-amino-2,4-dimethylphenol with 2-amino-4-t-butylphenol the title compound was prepared. NMR (DMSO) δ:(2 sets of signals) 1.05 (t, 3H), 1.29 (s, 9H), 4.03 (q, 2H), 6.91 (d, 1H), 7.13 (m, 1H), 7.56 (d, 1H), 8.76 (d, 1H), 10.39 (s, 1H), 12.68 (d, 1H).

Step 2. Ethyl 8-t-butyl-1,2-difluoro-4-oxo-4H-quino[2,3,4-i,j][1,4]benzoxazine-5-carboxylate Following the methods of Example 15 step 2 the ethyl 3-(5-t-butyl-2-hydroxyanilino)-2-(2,3,4,5-tetrafluorobenzoyl)acrylate from step 1 was reacted and the title product was obtained. NMR (DMSO) δ: 1.32 (t, 3H), 1.36 (s, 9H), 4.30 (q, 2H), 7.25 (d, 1H), 7.36 (m, 1H), 7.60 (m, 1H), 7.79 (d, 1H), 9.17 (s, 1H).

Step 3. Ethyl 1-(3-(N-t-butoxycarbonylamino)pyrrolidin-1-yl)-8-t-butyl-2-fluoro-4-oxo-4H-quino[2,3,4-i,j][1,4]benzoxazine-5-carboxylate Following the procedure of Example 15 step 4, ethyl 8-t-butyl-1,2-difluoro-4-oxo-4H-quino[2,3,4-i,j][1,4]benzoxazine-5-carboxylate from step 2 above was reacted with 3-(t-butoxycarbonylamino)pyrrolidine to afford the title compound, mp 120°–124° C. MS M/Z: 566 (M+H). NMR (CDCl$_3$) δ: 1.37 (s, (H), 1.46 (t, 3H), 1.48 (s, 9H), 1.92 (m, 1H), 2.24 (m, 1H), 3.48 (m, 1H), 3.63 (m, 1H), 3.72 (m, 1H), 3.93 (m, 1H), 4.33 (m, 1H), 4.45 (mq, 2H), 4.82 (m, 1H), 7.01 (d, 1H), 7.24 (dd, 1H), 7.37 (d, 1H), 7.63 (d, 1H), 8.90 (s, 1H). Analysis calculated for $C_{31}H_{36}FN_3O_6$: C, 65.82; H, 6.42; N, 7.43. Found: C, 65.66; H, 6.45; N, 7.38

Step 4. 1-(3-amino)pyrrolidin-1-yl)-8-t-butyl-2-fluoro-4-oxo-4H-quino[2,3,4-i,j][1,4]benzoxazine-5-carboxylic acid hydrochloride Ethyl 1-(3-(N-t-butoxycarbonylamino)pyrrolidin-1-yl)-8-t-butyl-2-fluoro-4-oxo-4H-quino[2,3,4-i,j][1,4]benzoxazine-5-carboxylate from step 3 above was hydrolyzed by the procedure of Example 18 step 2 to afford the title compound, mp 263°–266° C. MS M/Z: 438 (M+H). NMR (DMSO) δ: 1.36 (s, (H), 2.04 (m, 1H), 2.27 (m, 1H), 3.77 (m, 2H), 3.88 (m, 2H), 3.96 (m, 1H), 7.27 (d, 1H), 7.43 (dd, 1H), 7.53 (d, 1H), 7.87 (d, 1H), 9.28 (s, 1H): Analysis calculated for $C_{20}H_{25}ClFN_3O_4 \cdot H_2O$: C, 58.59; H, 5.53; N, 8.54. Found: C, 58.45; H, 5.28; N, 8.39.

EXAMPLE 22

1-(3-aminopyrrolidin-1-yl)-2,3-difluoro-4-oxo-4H-quino[2,3,4-i,j][1,4]benzoxazine-5-carboxylic acid hydrochloride Step 1: Ethyl 2,3,4,5,6-pentafluorobenzoyldiacetate To 10.3 g (0.423 mol) of magnesium powder was added 50 mL of ethanol and 1 mL of CCl$_4$, followed by dropwise addition under anhydrous conditions a solution of 67.7 g (0.423 mol) of malonic acid diethyl ester in 210 mL of ethanol. The reaction was then stirred at room temperature overnight, followed by heating under reflux conditions for 4 hours. After cooling, the solvent was removed under reduced pressure, and the residual ethanol was removed by azeotropic distillation with toluene (3×), then the residue was redissolved in 400 mL of dry ether.

To this solution cooled to 0° C. was added in a dropwise manner a solution of 100 g (0.434 mol) of pentafluorobenzoyl chloride in 120 mL of ether. After stirring for 1 hour in the cold, the reaction was then stirred at room temperature overnight. The mixture was then poured into 600 mL of 10% sulfuric acid solution. The organic layer was removed, and the aqueous solution was extracted with methylene chloride. The combined organic solvent was dried over anhydrous magnesium sulfate, filtered and evaporated, then the residue was further dried by adding and distilling off ethylene dichloride, chloroform and methylene chloride to afford 150.73 g of the diester as a golden liquid.

Step 2: Ethyl 2,3,4,5,6-pentafluorobenzoylacetate

To 150 g (0.423 mol) of the diester from step 1 was added 150 mL of water and 0.680 g of p-toluenesulfonic acid, and the mixture was heated at reflux for 3 hours. After cooling, the mixture was extracted with chloroform, which was washed with 5% potassium carbonate solution, dried over magnesium sulfate. The solvent was removed, and the residue was further dried by adding and distilling off ethylene dichloride, chloroform and methylene chloride, followed by further drying under vacuum to afford 95.96 g of the title compound as a golden liquid. MS M/Z: 300 (M+NH$_4$). Other spectra confirmed the structure.

Step 3. Ethyl 4-(3-acetamidopyrrolidin-1-yl)-2,3,5,6-tetrafluorobenzoylacetate

To 2.62 g (20.4 mmol) of 3-acetamidopyrrolidine dissolved in 50 mL of pyridine and cooled to 0° C. was added 2.06 g (20.4 mmol) of triethylamine and 5.24 g (18.6 mmol) of ethyl 2,3,4,5,6-pentafluorobenzoylacetate, from step 2 above. The solution was stirred at 0° C. for 1 hour, then at room temperature overnight. The solvent was removed by evaporation under vacuum and the residue was dissolved in chloroform, which was washed with 0.5N HCl and 5% potassium carbonate solution. The organic layer was dried over magnesium sulfate, filtered, and evaporated. The residue was further dried by adding and distilling off ethylene dichloride, chloroform and methylene, followed by further drying under vacuum. The crystalline residue was washed with hexane and dried to afford 6.8 g of the title compound as a tan solid, mp 90°–92° C. MS M/Z: 391 (M+H). IR (CDCl$_3$): 1635, 1680, 1740 cm$^{-1}$. NMR (CDCl$_3$) d: 1.26 (m, 3H), 2.00 (m, 5H), 2.22 (m, 2H), 3.54 (m, 1H), 3.77 (m, 2H), 3.85 (m, 1H), 3.98 (m, 1H), 4.22 (m, 2H), 5.75 (m, 1H). Analysis calculated for C17H$_{18}$F$_4$N$_2$O$_4$: C, 52.31; H, 4.65; N, 7.18. Found: C, 52.47; H, 4.67; N, 7.33.

Step 4. Ethyl 3-(2-hydroxyanilino)-2-(4-(3-acetamidopyrrolidin-1-yl)-2,3,5,6-tetrafluorobenzoyl)acrylate To a 6.82 g (17.5 mmol) sample of the beta-ketoester from step 3 was added 3.89 g (26.1 mmol) of triethyl orthoformate and 8.00 g (78 mmol) of acetic anhydride, and the reaction was stirred at 130° C. for 2.5 hours. The volatile materials were then removed under reduced pressure, and toluene was added and distilled from the residue to remove any remaining reagents. The dried residue was then dissolved in 150 mL of methylene chloride and 1.91 g (17.5 mmol) of o-aminophenol was added. The reaction was stirred at room temperature overnight. The solvent was removed under reduced pressure, and the residue was washed with ether, filtered and added to afford 7.59 g of the title compound as a yellow solid, mp 221° C. (dec). MS M/Z: 510 (M+H). IR (KBr): 1623, 1643, 1684 cm$^{-1}$. NMR (DMSO) d: 1.10 (m, 3H), 1.82 (m, 3H), 2.05 (m, 2H), 3.64 (m, 2H), 3.80 (m, 4H), 4.04 (m, 2H), 6.95 (m, 1H), 7.10 (m, 1H), 7.58 (m, 1H), 8.16 (m, 1H), 8.65 (m, 1H), 10.60 (m, 1H), 12.73 (m, 1H). Analysis calculated for $C_{24}H_{23}F_4N_3O_5$: C, 56.58; H, 4.55; N, 8.25. Found: C, 56.30; H, 4.63; N, 8.22.

Step 5. Ethyl 1-(3-(N-acetamido)pyrrolidin-1-yl)-2,3-difluoro-4-oxo-4H-quino[2,3,4-i,j][1,4]benzoxazine-5-carboxylate A 6.76 g (48.9 mmol) portion of potassium carbonate was suspended in 100 mL of dry DMF and 7.55 g (14.8 mmol) of the, acrylate derivative from step 4 was added. The suspension was stirred at room temperature overnight, then at 100° C. for 2 hours. The suspension was diluted with chloroform and the insoluble materials removed by filtration. The solvents were removed by co-distillation with toluene, and the residue was washed with water, then redissolved in chloroform and washed with 0.5N HCl and 5% potassium carbonate solution. The organic layer was dried over magnesium sulfate, and the solvent was removed by co-distillation with methylene chloride under reduced pressure. The residue was washed with ether and added to afford 5.68 g of the title product as a yellow solid, mp 246°–8° C. MS M/Z: 470 (M+H). IR (KBr): 1640, 1670, 1723 cm$^{-1}$. NMR (CDCl$_3$) d: 1.38 (m, 3H), 2.10 (M, 3H), 2.13 (m, 3H), 3.62 (m, 2H), 4.02 (m, 2H), 4.33 (m, 2H), 4.62 (m, 1H), 6.88 (m, 1H), 6.95 (m, 1H), 7.10 (m, 1H), 7.20 (m, 1H), 7.53 (m, 1H), 8.20 (m, 1H). Analysis calculated for $C_{24}H_{21}F_2N_3O_5 \cdot \frac{1}{2} H_2O$: C, 60.25; H, 4.63; N, 8.78. Found: C, 60.34; H, 4.32; N, 8.72.

Step 6. 1-(3-aminopyrrolidin-1-yl)-2,3-difluoro-4-oxo-4H-quino[2,3,4-i,j][1,4]benzoxazine-5-carboxylic acid hydrochloride To a 3.03 g (6.45 mmol) sample of the protected ester from step 5 was added 300 mL of 2N HCl and the mixture was stirred at 90° C. for 66 hr. After cooling, the solution was diluted with a small amount of water and ethanol. The solvents were then removed under vacuum, and ethanol then methanol were added and distilled from the residue to remove water and HCl. After drying 2.18 g of the title compound as an orange solid was obtained, mp>280° C. MS M/Z: 400 (M+H). IR (KBr): 1640, 1720 cm$^{-1}$. NMR (DMSO) d: 2.05 (m, 2H), 2.26 (m, 2H), 3.32 (m, 2H), 4.0 (m, 1H), 7.27 (m, 2H), 7.38 (m, 1H), 7.92 (m, 1H), 8.38 (m, 2H), 9.03 (s, 1H). Analysis calculated for $C_{20}H_{16Cl}F_2N_3O_4 \cdot \frac{1}{2} H_2O$: C, 54.00; H, 3.85; N, 9.45. Found: C, 53.67; H, 3.60; N, 9.30.

EXAMPLE 23

2,3-difluoro-1-(3-norvalylaminopyrrolidin-1-yl)-4-oxo-4H-quino[2,3,4-i,j][1,4]benzoxazine-5-carboxylic acid hydrochloride Step 1: 1-(t-N-butyloxycarbonyl-norvalylaminopyrrolidin-1-yl)-2,3-difluoro-4-oxo-4H-quino[2,3,4-i,j][1,4]benzoxazine-5-carboxylic acid Following the procedure of Example 8, substituting 1-(3-aminopyrrolidin-1-yl)-2,3-difluoro-4-oxo-4H-quino[2,3,4-i,j][1,4]benzoxazine-5-carboxylic acid hydrochloride, prepared in Example 22 above, for the 1-(3-aminopyrrolidin-1-yl)-2-fluoro-4-oxo-4H-quino[2,3,4-i,j][1,4]benzoxazine-5-carboxylic acid hydrochloride of Example 8, the boc protected title compound was compound was prepared, mp 219° C. (dec). MS M/Z: 599 (M+H). IR (KBr): 1635, 1730 cm$^{-1}$. NMR (CDCl$_3$) d: 0.95 (m, 3H), 1.42 (m, 9H), 1.82 (m, 2H), 2.13 (m, 2H), 3.75 (m, 2H), 4.10 (m, 2H), 4.60 (m, 1H), 5.12 (m, 1H), 7.11 (m, 2H), 7.33 (m, 2H), 8.78 (m, 1H), 14.7 (m, 1H). Analysis calculated for $C_{30}H_{32}F_2N_4O_7 \cdot \frac{1}{2} H_2O$: C, 59.30; H, 5.47; N, 9.22. Found: C, 59.33; H, 5.25; N, 9.28.

Step 2: 2,3-difluoro-1-(3-norvalylaminopyrrolidin-1-yl)-4-oxo-4H-quino[2,3,4-i,j][1,4]benzoxazine-5-carboxylic acid hydrochloride The boc protected compound from step 1 was hydrolyzed and converted to the HCl salt by the procedure of Example 8 step 2. Mp 203°–5° C. MS M/Z: 499 (M+H). IR (KBr): 1635, 1680, 1720 cm$^{-1}$. NMR (CD$_3$OD) d: 0.95 (m, 2H), 1.00 (m, 3H), 1.45 (m, 2H), 1.83 (m, 2H), 2.05 (, 1H), 2.26 (m, 1H), 3.70 (m, 1H), 3.85 (m, 2H), 4.10 (m, 2H), 4.48 (m, 2H), 7.12 (m, 1H), 7.20 (m, 1H), 7.33 (m, 1H), 7.60 (m, 1H), 8.92 (m, 1H).

EXAMPLE 24

2-fluoro-1-((3R)-3-norvalylaminopyrrolidin-1-yl)-4-oxo-4H-quino[2,3,4-i,j][1,4]benzoxazine-5-carboxylic acid hydrochloride Step 1: 1-((3R)-t-N-butyloxycarbonyl-norvalylaminopyrrolidin-1-yl))-2-fluoro-4-oxo-4H-quino[2,3,4-i,j][1,4]benzoxazine-5-carboxylic acid Following the procedure of Example 8 step 1 and substituting 1-((3R)-3-aminopyrrolidin-1-yl)-2-fluoro-4-oxo-4H-quino[2,3,4-i,j][1,4]benzoxazine-5-carboxylic acid hydrochloride, prepared in Example 17 above, for the 1-(3-aminopyrrolidin-1-yl)-2-fluoro-4-oxo-4H-quino[2,3,4-i,j][1,4]benzoxazine-5-carboxylic acid hydrochloride of Example 8, the boc protected title compound was prepared, mp 262°–4° C. (dec). MS M/Z: 581 (M+H). IR (KBr): 1630, 1710 cm$^{-1}$. NMR (DMSO) d: 0.85 (m, 3H), 1.27 (m, 2H), 1.36 (m, 9H), 1.50 (m, 2H), 1.85 (m, 2H), 2.11 (m, 2H), 3.53 (m, 1H), 3.90 (m, 3H), 4.32 (m, 1H), 6.80 (m, 1H), 7.27 (m, 1H), 7.36 (m, 1H), 7.50 (m, 1H), 8.00 (m, 1H), 8.15 (m, 1H), 9.10 (m, 1H), 14.94 (m, 1H). Analysis calculated for $C_{30}H_{33}FN_4O_7 \cdot \frac{1}{3} H_2O$: C, 61.42; H, 5.78; N, 9.55. Found: C, 61.57; H, 5.72; N, 9.53.

Step 2: 2-fluoro-1-(3R)-3-norvalylaminopyrrolidin-1-yl)-4-oxo-4H-quino[2,3,4-i,j][1,4]benzoxazine-5-carboxylic acid hydrochloride.

The boc protected compound from step 1 was hydrolyzed and converted to the HCl salt by the procedure of Example 8 step 2. Mp 198°–200° C. MS M/Z: 481 (M+H). IR (KBr): 1630, 1680, 1720 cm$^{-1}$. NMR (DMSO) d: 0.90 (m, 3H), 1.34 (m, 2H), 1.70 (m, 2H), 1.90 (m, 1H), 2.18 (m, 1H), 3.60 (m, 1H), 3.75 (m, 2H), 3.92 (m, 1H), 4.03 (m, 1H), 4.36 (m, 1H), 7.33 (m, 4H), 7.48 (m, 1H), 8.00 (m, 1H), 8.95 (m, 1H), 9.10 (m, 1H). Analysis calculated for $C_{25}H_{26}ClFN_4O_5 \cdot H_2O$: C, 56.12; H, 5.27; N, 10.47. Found: C, 56.11; H, 5.10; N, 10.28.

EXAMPLE 25

2-fluoro-1-((3S)-3-norvalylaminopyrrolidin-1-yl)-4-oxo-4H-quino[2,3,4-i,j][1,4]benzoxazine-5-carboxylic acid hydrochloride Step 1: 1-((3S)-t-N-butyloxycarbonyl-norvalylaminopyrrolidin-1-yl))-2-fluoro-4-oxo-4H-quino[2,3,4-i,j][1,4]benzoxazine-5-carboxylic acid Following the procedure of Example 8 step 1, substituting 1-((3S)-3-aminopyrrolidin-1-yl)-2-fluoro-4-oxo-4H-quino[2,3,4-i,j][1,4]benzoxazine-5-carboxylic acid hydrochloride., prepared in Example 17 above, for the 1-(3-aminopyrrolidin-1-yl)-2-fluoro-4-oxo-4H-quino[2,3,4-i,j][1,4]benzoxaxine-5-carboxylic acid hydrochloride of Example 8, the boc protected title compound was prepared, mp 235° C. MS M/Z: 581 (M+H). IR (KBr): 1630, 1680, 1720 cm$^{-1}$. NMR (DMSO) d: 0.81 (m, 3H), 1.13 (m, 2H), 1.36 (m, 9H), 1.46 (m, 2H), 1.90 (m, 2H), 2.10 (m, 2H), 3.50 (m, 1H), 3.74 (m, 1H), 3.90 (m, 3H), 4.30 (m, 1H), 6.80 (m, 1H), 7.25 (m, 1H), 7.35 (m, 1H), 7.47 (m, 1H), 8.00 (m, 1H), 8.13 (m, 1H), 9.08 (m, 1H), 14.92 (m, 1H). Analysis calculated for $C_{30}H_{33}FN_4O_7 \cdot \frac{1}{2} H_2O$: C, 61.11; H, 5.81; N, 9.50. Found: C, 61.07; H, 5.69; N, 9.49.

Step 2: 2-fluoro-1-((3S)-3-norvalylaminopyrrolidin-1-yl)-4-oxo-4H-quino[2,3,4-i,j][1,4]benzoxazine-5-carboxylic acid hydrochloride.

The boc protected compound from step 1 was hydrolyzed and converted to the HCl salt by the procedure of Example 8 step 2. Mp 210°–2° C. MS M/Z: 481 (M+H). IR (KBr): 1630, 1680, 1720 cm$^{-1}$. NMR (DMSO) d: 0.82 (m, 3H), 1.28 (m, 2H), 1.65 (m, 2H), 1.96 (m, 1H), 2.15 (m, 1H), 3.53 (m, 1H), 3.74 (m, 2H), 3.95 (m, 1H), 4.34 (m, 1H), 7.25 (m, 2H), 7.34 (m, 1H), 7.48 (m, 1H), 8.01 (m, 1H), 8.90 (m, 1H), 9.10 (m, 1H). Analysis calculated for $C_{25}H_{26}ClFN_4O_5 \cdot H_2O$: C, 56.12; H, 5.27; N, 10.47. Found: C, 56.11; H, 5.10; N, 10.28.

EXAMPLE 26

2-fluoro-9-methyl-1-((3R)-3-norvalylaminopyrrolidin-1-yl)-4-oxo-4H-quino[2,3,4-i,j][1,4]benzoxazine-5-carboxylic acid hydrochloride Step 1: 1-((3R)-t-N-butyloxycarbonyl-norvalylaminopyrrolidin-1-yl))-2-fluoro-9-methyl-4-oxo-4H-quino[2,3,4-i,j][1,4]benzoxazine-5-carboxylic acid.

Following the procedure of Example 8 step 1, substituting 1-((3R)-3-aminopyrrolidin-1-yl)-2-fluoro-9-methyl-4-oxo-4H-quino[2,3,4-i,j][1,4]benzoxazine-5-carboxylic acid hydrochloride, prepared in Example 19 above, for the 1-(3-aminopyrrolidin-1-yl)-2-fluoro-4-oxo-4H-quino[2,3,4-i,j][1,4]benzoxazine-5-carboxylic acid hydrochloride of Example 8, the boc protected title compound was prepared, mp 220° C. (dec). MS M/Z: 595 (M+H). IR (CDCl$_3$): 1630, 1670, 1710 cm$^{-1}$. NMR (CDCl$_3$) d: 0.96 (m, 3H), 1.43 (m, 12H), 1.85 (m, 2H), 2.13 (m, 2H), 2.35 (m, 3H), 3.70 (m, 2H), 4.03 (m, 2H), 4.18 (m, 1H), 4.60 (m, 1H), 5.13 (m, 1H), 6.83 (m, 1H), 6.93 (m, 1H), 7.16 (m, 1H), 7.39 (m, 1H), 8.83 (m, 1H), 14.93 (m, 1H). Analysis calculated for $C_{31}H_{35}FN_4O_7 \cdot \frac{1}{3} H_2O$: C, 61.98; H, 5.98; N, 9.33. Found: C, 62.00; H, 5.89; N, 9.41.

Step 2: 2-fluoro-9-methyl-1-((3R)-3-norvalylaminopyrrolidin-1-yl)-4-oxo-4H-quino[2,3,4-i,j][1,4]benzoxazine-5-carboxylic acid hydrochloride.

The boc protected compound from step 1 is hydrolyzed and converted to the HCl salt by the procedure of Example 8 step 2.

EXAMPLE 27

1-(3-aminopyrrolidin-1-yl)-8-ethylsulfonyl-2-fluoro-4-oxo-4H-quino[2,3,4-i,j][1,4]benzoxazine-5-carboxylic acid hydrochloride Step 1: 1,2-difluoro-8-ethylsulfonyl-4-oxo-4H-quino[2,3,4-i,j][1,4]benzoxazine-5-carboxylic acid Following the procedures of Examples 2 and 3, substituting 2-amino-4-ethylsulfonylphenol for the 2-hydroxy-5-nitroaniline of Example 2 and substituting the resulting product for the starting material of Example 3, the title compound was prepared, mp>290° C. MS M/Z: 436 (M+H). IR (KBr): 1630, 1710 cm$^{-1}$. NMR (DMSO) d: 1.15 (m, 3H), 1.32 (m, 3H), 4.31 (m, 2H), 3.45 (m, 2H), 7.53 (m, 1H), 7.65 (m, 1H), 7.76 (m, 1H), 8.35 (m, 1H), 9.18 (s, 1H). Analysis calculated for $C_{20}H_{15}F_2NO_6 \cdot \frac{1}{3} H_2O$: C, 54.42; H, 3.58; N, 3.17. Found: C, 54.54; H, 3.44; N, 3.46.

Step 2: Ethyl 1-(3-(t-butyloxycarbonylamino)pyrrolidin-1-yl)-8-ethylsulfonyl-2-fluoro-4-oxo-4H-quino[2,3,4-i,j][1,4]benzoxazine-5-carboxylate Following the procedure of Example 15 step 4, substituting ethyl 1,2-difluoro-8-ethylsulfonyl-4-oxo-4H-quino[2,3,4-i,j][1,4]benzoxazine-5-carboxylate from step 1 above for the benzoxazine of Example 15, the title compound was prepared, mp 132°–5° C. MS M/Z: 602 (M+H). IR (KBr): 1620, 1700, 1720 cm$^{-1}$. NMR (CDCl$_3$) d: 1.35 (m, 3H), 1.45 (m, 12H), 1.92 (m, 2H), 2.23 (m, 2H), 3.20 (m, 2H), 3.51 (m, 1H), 3.68 (m, 1H), 3.85 (m, 1H), 3.95 (m, 1H), 4.45 (m, 2H), 7.20 (m, 1H), 7.62 (m, 1H), 7.72 (m, 1H), 7.78 (m, 1H), 8.78 (m, 1H). Analysis calculated for $C_{29}H_{32}FN_3O_5 \cdot \frac{1}{2} H_2O$: C, 57.03; H, 5.45; N, 6.88. Found: C, 56.90; H, 5.28; N, 6.78.

Step 3 1-(3-aminopyrrolidin-1-yl)-8-ethylsulfonyl-2-fluoro-4-oxo-4H-quino[2,3,4-i,j][1,4]benzoxazine-5-carboxylic acid hydrochloride.

The boc protected compound from step 2 was hydrolyzed and converted to the HCl salt by the procedure of Example 18 step 2, mp 222°–5° C. MS M/Z: 474 (M+H). IR (KBr): 1630, 1720 cm$^{-1}$. NMR (DMSO) d: 1.15 (m, 3H), 2.05 (m, 2H), 2.25 (m, 2H), 3.50 (m, 2H), 3.78 (m, 2H), 3.90 (m, 2H), 4.00 (m, 1H), 7.75 (m, 2H), 7.85 (m, 1H), 8.45 (m, 1H), 9.20 (m, 1H). Analysis calculated for $C_{22}H_{21}FN_3O_6S \cdot H_2O$: C, 50.04; H, 4.39; N, 7.96. Found: C, 49.97; H, 4.20; N, 7.61.

EXAMPLE 28

8-ethylsulfonyl-2-fluoro-1-(3-norvalylaminopyrrolidin-1-yl)-4-oxo-4H-quino[2,3,4-i,j][1,4]benzoxazine-5-carboxylic acid hydrochloride Step 1: 1-(t-N-butyloxycarbonyl-norvalylaminopyrrolidin-1-yl)-2-fluoro-8-ethylsulfonyl-4-oxo-4H-quino[2,3,4-i,j][1,4]benzoxazine-5-carboxylic acid Following the procedure of Example 8 step 1, substituting 1-(3-aminopyrrolidin-1-yl)-8-ethylsulfonyl-2-fluoro-4-oxo-4H-quino[2,3,4-i,j][1,4]benzoxazine-5-carboxylic acid hydrochloride, from example 27 above, for the benzoxazine compound of Example 8, the boc-protected title compound was prepared, mp 223° C. (dec). MS M/Z: 474 (M+H). IR (KBr): 1630, 1720 cm$^{-1}$. NMR (DMSO) d: 0.83 (m, 3H), 1.15 (m, 3H), 1.27 (m, 2H), 1.35 (m, 9H), 1.47 (m, 2H), 1.87 (m, 2H), 2.10 (m, 2H), 3.46 (m, 2H), 3.51 (m, 1H), 3.77 (m, 1H), 3.87 (m, 1H), 3.97 (m, 1H), 6.78 (m, 1H), 7.45 (m, 1H), 7.51 (m, 1H), 7.81 (m, 1H), 8.15 (m, 1H), 8.42 (m, 1H), 9.27 (m, 1H), 14.82 (m, 1H). Analysis calculated for $C_{32}H_{37}FN_4O_9S \cdot H_2O$: C, 57.13; H, 5.54; N, 8.33. Found: C, 57.02; H, 5.39; N, 8.19.

Step 2: 8-Ethylsulfonyl-2-fluoro-1-(3-norvalylaminopyrrolidin-1-yl)-4-oxo-4H-quino[2,3,4-i,j][1,4]benzoxezine-5-carboxylic acid hydrochloride.

Following the procedure of Example 8 step 2, substituting the compound from step 1 above for the boc-protected compound of example 8, the title compound was prepared, mp 218°–20° C. MS M/Z: 573 (M+H). IR (KBr): 1630, 1680, 1720 cm$^{-1}$. NMR (DMSO) d: 0.85 (m, 3H), 1.15 (m, 4H), 1.30 (m, 2H), 1.67 (m, 2H), 1.92 (m, 2H), 2.15 (m, 1H), 3.50 (m, 2H), 3.55 (m, 1H), 3.75 (m, 2H), 3.95 (m, 1H), 4.04 (m, 1H), 4.36 (m, 1H), 7.52 (m, 2H), 7.82 (1H), 8.55 (m, 1H), 8.98 (m, 1H), 9.30 (m, 1H). Analysis calculated for $C_{27}H_{30}ClFN_4O_7S$: C, 53.24; H, 4.96; N, 9.20. Found: C, 53.01; H, 5.02; N, 8.76.

EXAMPLE 29

1-(3-aminopyrrolidin-1-yl)-2-fluoro-5-(1-morpholinocarbonyl)-4-oxo-4H-quino[2,3,4-i,j][1,4]benzoxazine trifluoracetate salt Step 1. 1,2-difluoro-5-(1-morpholinocarbonyl)-4-oxo-4H-quino[2,3,4-i,j][1,4]benzoxazine Morpholine 0.281 mL (3.2 mmol) was dissolved in 10 mL of methylene cholride at room temperature in dry nitrogen. 1.6 mL (3.2 mmol) of trimethylaluminum was then added dropwise and the mixture was stirred for 30 min. A 1 g (2.9 mmol) sample of ethyl 1,2-difluoro-4-oxo-4H-quino[2,3,4-i,j][1,4]benzoxazine-5-carboxylate, from example 3, was dissolved in 25 mL of methylene chloride and added to the first solution and stirred at room temperature overnight. The reaction was quenched with 0.1M HCl and the mixture was extracted with methylene choride. The organic layer was dried and the solvent was removed to afford the title compound as a solid.

Step 2. 1-(3-aminopyrrolidin-1-yl)-2-fluoro-5-(1-moroholinocarbonyl)-4-oxo-4H-quino[2,3,4-i,j][1,4]benzoxazine trifluoracetate salt Following the procedure as described in *J. Heterocyclic Chem.* 24:453–456 (1987), substituting the amide from step 1 above for the ethyl 1,2-difluoro-4-oxo-4H-quino[2,3,4-i,j][1,4]benzoxazine-5-carboxylate of that reaction, the title compound was prepared. The product was dissoved in trifluoroacetic acid, and the excess solvent was removed to yield the title compound as the salt as a yellow solid, mp>270° C. MS M/Z: 451 (M+H). IR (KBr): 1630, 1710 cm$^{-1}$. NMR (DMSO) d: 2.00 (m, 1H), 2.26 (m, 1H), 3.28 (m, 2H), 3.57 (m, 4H), 3.63 (m, 4H), 3.69 (m, 1H), 3.78 (m, 1H), 3.88 (m, 1H), 7.17 (m, 1H), 7.23 (d, 2H), 7.35 (d, 1H), 7.90 (d, 1H), 8.24 (s, 2H), 8.70 (s, 1H).

EXAMPLE 30

1-(3-aminopyrrolidin-1-yl)-2-fluoro-4-oxo-4H-quino[2,3,4-i,j][1,4]benzoxazine-5-(N-2,4-difluorphenyl)carboxamide hydrochloride Step 1. 1,2-difluoro-4-oxo-4H-quino[2,3,4-i,j][1,4]benzoxazine-5-(N-2,4-difluorphenyl)carboxamide 2,4-Difluoroaniline (0.34 mL, 3.2 mmol) was dissolved in 10 mL of methylene cholride at room temperature in dry nitrogen. 1.6 mL (3.2 mmol) of trimethylaluminum was then added dropwise and the mixture was stirred for 30 min. A 1 g (2.9 mmol) sample of ethyl 1,2-difluoro-4-oxo-4H-quino[2,3,4-i,j][1,4]benzoxazine-5-carboxylate, from example 3, was dissolved in 25 mL of methylene chloride and added to the first solution and stirred at room temperature for 20 hours. The precipitated product was collected, washed with methylene chloride and ethanol and dried to afford 0.56 g of the title compound as a light yellow solid.

Step 2. 1-(3-aminopyrrolidin-1-yl)-2-fluoro-4-oxo-4H-quino[2,3,4-i,j][1,4]benzoxazine-5-(N-2,4-difluorphenyl)carboxamide hydrochloride Following the procedure as described in *J. Heterocyclic Chem.* 24:453–456 (1987), substituting the amide from step 1 above for the ethyl 1,2-difluoro-4-oxo-4H-quino[2,3,4-i,j][1,4]benzoxazine-5-carboxylate of that reaction, the title compound was prepared. The product was dissoved in hydrochloric acid, and the excess solvent was removed to yield the title compound as the salt as a yellow solid, mp>270° C. MS M/Z: 493 (M+H). IR (KBr): 1520, 1620, 1680 cm$^{-1}$. NMR (DMSO) d: 2.04 (m, 1H), 2.26 (m, 1H), 3.22 (m, 1H), 3.41 (m, 1H), 3.72 (m, 1H), 3.86 (m, 2H), 7.10 (m, 1H), 7.23 (m, 1H), 7.32 (m, 1H), 7.37 (m, 1H), 7.46 (d, 1H), 7.84 (d, 1H), 8.48 (m, 1H), 8.57 (s, 1H), 9.08 (s, 1H).

EXAMPLE 31

1((2S,4S)-4-amino-2-methylpyrrolidin-1-yl)-8,10-dimethyl-2-fluoro-4-oxo-4H-quino[2,3,4-i,j][1,4]benzoxazine-5-carboxylic acid hydrochloride Step 1 (2S,4S)-4-acetamido-2-methylpyrrolidine hydrochloride (2S,4S)-4-acetamido-1-(t-butoxycarbonyl)-2-methylpyrrolidine, prepared as described by Rosen, T., et al., *J. Med. Chem.*, 31, 1598–1611 (1988), is dissolved in 30 mL of 4N HCl in dioxane and stirred at room temperature for 24 hours to remove the boc group. The solvent is removed by evaporation to give the hydrochloride salt of this compound Step 2. (2S,4S)-4-acetamido-1-benzyl-2-methylpyrrolidine (2S,4S)-4-acetamido-2-methylpyrrolidine hydrochloride from the previous step is suspended in methylene chloride, t-ethylamine and benzyl bromide are added and the mixture heated at reflux. The product is obtained after washing and evaporation of the solvent.

Step 3. (2S,4S)-4-amino-1-benzyl-2-methylpyrrolidine hydrochloride

The acetyl group is removed from (2S,4S)-4-acetamido-1-benzyl-2-methylpyrrolidine by heating with 6N HCl. Removal of the solvent gives the solid product.

Step 4. (2S,4S)-1-benzyl-4-t-butoxycarbonylamino-2-methylpyrrolidine

The (2S,4S)-4-amino-1-benzyl-2-methylpyrrolidine hydrochloride is treated with triethylamine and di-t-butyl dicarbonate to protect the 4-amino group.

Step 5. (2S,4S)-4-t-butoxycarbonylamino-2-methylpyrrolidine

The benzyl protecting group is removed from (2S,4S)-1-benzyl-4-t-butoxycarbonylamino-2-methylpyrrolidine by hydrogenolysis in methanol with 10% Pd/C, to give the title compound.

Step 6. 1-((2S,4S)-4-t-butoxycarbonylamino-2-methylpyrrolidin-1-yl)-8,10-dimethyl-2-fluoro-4-oxo-4H-quino[2,3,4-i,j][1,4]benzoxazine-5-carboxylic acid Following the procedure of Example 15 Step 4, but substituting (2S,4S)-4-t-butoxycarbonylamino-2-methylpyrrolidine for the 3-(t-butoxycarbonylamino)pyrrolidine and reacting it with 1,2-difluoro-8,10 dimethyl-4-oxo-4H-quino[2,3,4-i,j][1,4]benzoxazine-5-carboxylic acid, the title compound is prepared.

Step 7. 1-((2S,4S)-4-amino-2-methylpyrrolidin-1-yl)-8,10-dimethyl-2-fluoro-4-oxo-4H-quino[2,3,4-i,j][1,4]benzoxazine-5-carboxylic acid hydrochloride The 1-((2S,4S)-4-t-butoxycarbonylamino-2-methylpyrrolidin-1-yl)-8,10-dimethyl-2-fluoro-4-oxo-4H-quino[2,3,4-i,j][1,4]benzoxazine-5-carboxylic acid from the previous step is deprotected by the procedure of Example 8 step 2, and the title product is isolated as the salt.

EXAMPLE 32

1(3-aminopyrrolidin-1-yl)-2-fluoro-8,9-methylenedioxy-4-oxo-4H-quino[2,3,4-i,j][1,4]benzoxazine-5-carboxylic acid hydrochloride Step 1: Ethyl 1,2-difluoro-8,9-methylenedioxy-4-oxo-4H-quino[2,3,4-i,j][1,4]benzoxazine-5-carboxylate Following the procedures of Examples 2 and 3, substituting 2-amino-4,5-methylenedioxyphenol (prepared via the method of D. G. Orphanos and A. Taurins *Canadian J.*

*Chem.* 44, 1875–9, (1966)) for the 2-hydroxy-5-nitroaniline of Example 2 and substituting the resulting product for the starting material of Example 3, the title compound was prepared, MS M/Z: 388 (M+H). NMR (CDCl$_3$) d: 1.43 (m, 3H), 4.43 (m, 2H), 6.09 (s, 2H), 6.72 (s, 1H), 7.00 (s, 1H), 7.80 (m, 1H), 8.80 (s, 1H).

Step 2: Ethyl 1-(3-(t-butyloxycarbonylamino)pyrrolidin-1-yl)-2-fluoro-8,9-methylenedioxy-4-oxo-4H-ouino[2,3,4-i,j][1,4]benzoxazine-5-carboxylate Following the procedure of Example 15 step 4, substituting ethyl 1,2-difluoro-8,9-methylenedioxy-4-oxo-4H-quino[2,3,4-i,j][1,4]benzoxazine-5-carboxylate from step 1 above for the benzoxazine of Example 15, the title compound was prepared, mp 206°–9° C. MS M/Z: 555 (M+H). IR (KBr): 1620, 1720 cm$^{-1}$. NMR (CDCl$_3$) d: 1.44 (, 3H), 1.48 (s, 9H), 1.92 (m, 1H), 2.22 (m, 1H), 3.48 (m, 1H), 3.62 (m, 1H), 3.78 (m, 1H), 3.87 (m, 1H), 4.32 (m, 1H), 4.43 (q, 2H), 4.93 (m, 1H), 6.05 (s, 2H), 6.6 (s, 1H), 6.91 (s, 1H), 7.63 (d, 1H, J=13 Hz), 8.67 (s, 1H).

Step 3: 1-(3-aminopyrrolidin-1-yl)-2-fluoro-8,9-methylenedioxy-4-oxo-4H-quino[2,3,4-i,j][1,4]benzoxazine-5-carboxylic acid hydrochloride The boc protected compound from step 2 was hydrolyzed and converted to the HCl salt by the procedure of Example 8 step 2, mp>270° C. MS M/Z: 426 (M+H). IR (KBr): 1620, 1720 cm$^{-1}$. NMR (DMSO) d: 2.04 (m, 1H), 2.27 (m, 1H), 3.84 (m, 5H), 6.15 (s, 2H), 7.10 (s, 1H), 7.48 (d, 1H, J=13 Hz), 7.82 (s, 1H), 8.35 (br s, 3H), 9.00 (s, 1H). Analysis calculated for C$_{21}$H$_{17}$ClFN$_3$O$_6$·H$_2$O: C, 52.56; H, 3.57; N, 8.76. Found: C, 52.39; H, 3.29; N, 8.43.

EXAMPLE 33

1-((2S,4S)-4-amino-2-methylpyrrolidin-1-yl)-2-fluoro-8-methyl-4-oxo-4H-quino[2,3,4-i,j][1,4]benzoxazine-5-carboxylic acid hydrochloride By repeating Example 31 and substituting 1,2-difluoro-8-methyl-4-oxo-4H-quino[2,3,4-i,j][1,4]benzoxazine-5-carboxylic acid for the 1,2-difluoro-8,10 dimethyl-4-oxo-4H-quino[2,3,4-i,j][1,4]benzoxazine-5-carboxylic acid, the title compound is prepared.

EXAMPLE 34

1-((2S,4S)-4-amino-2-methylpyrrolidin-1-yl)-2-fluoro-4-oxo-4H-quino[2,3,4-i,j][1,4]benzoxazine-5-carboxylic acid hydrochloride By repeating Example 31 and substituting 1,2-difluoro-4-oxo-4H-quino[2,3,4-i,j][1,4]benzoxazine-5-carboxylic acid for the 1,2-difluoro-8,10 dimethyl-4-oxo-4H-quino[2,3,4-i,j][1,4]benzoxazine-5-carboxylic acid, the title compound may be prepared.

EXAMPLE 35

Ethyl 1-(3-aminopyrrolidin-1-yl)-2-fluoro-8,9-methylenedioxy-4-oxo-4H-quino[2,3,4-i,j][1,4]benzoxazine-5-carboxylate By hydrolyzing the boc-protecting group from ethyl 1-(3-(t-butyloxycarbonylamino)pyrrolidin-1-yl)-2-fluoro-8,9-methylenedioxy-4-oxo-4H-quino[2,3,4-i,j][1,4]benzoxazine-5-carboxylate, from Example 32 step 2 above, with trifluoroacetic acid, the title compound was prepared, mp 205° C. (dec). MS M/Z: 454 (M+H). IR (KBr): 1620, 1690, 1720 cm$^{-1}$. NMR (CDCl$_3$) d: 1.43 (m, 3H), 1.76 (m, 1H), 2.15 (m, 1H), 3.40 (m, 1H), 3.69 (m, 2H), 3.85 (m, 2H), 4.42 (m, 2H), 6.04 (s, 2H), 6.58 (s, 1H), 6.92 (s, 1H), 7.60 (s, 1H), 8.65 (s, 1H). Analysis calculated for C$_{23}$H$_{20}$FN$_3$O$_6$: C, 60.93; H, 4.45; N, 9.27; F, 4.19. Found: C, 60.18; H, 4.43; N, 9.13; F, 4.54.

EXAMPLE 36

3-amino-1-(3-aminopyrrolidin-1-yl)-2-fluoro-4-oxo-4H-quino[2,3,4-i,j][1,4]benzoxazine-5-carboxylic acid Step 1. 2-Methoxyethoxymethoxyaniline.

2-Nitrophenol is reacted with methoxyethoxymethyl chloride in the presence of a base, for example N,N-diisopropylethyl amine, to give 1-methoxyethoxymethoxy-2-nitrobenzene. This compound is hydrogenated with gaseous hydrogen in the presence of a catalyst, such as nickel, palladium, platinum, or chemically with, for example SnCl$_2$ and ethanol, to give the title compound.

Step 2. Ethyl 2-(4-(3-acetamidopyrrolidin-1-yl)-3-(2-methoxyethoxymethoxyanilino)2,3,5,6tetrafluorobenzoyl)acrylate Ethyl 4-(3-acetamidopyrrolidin-1-yl)-2,3,5,6-tetrafluorobenzoylacetate is reacted with 2-methoxyethoxymethoxyaniline by a procedure similar to that of Example 22 step 4 to prepare the title compound.

Step 3. Ethyl 7-(3-acetamidopyrrolidin-1-yl)-5,6-difluoro-1-(2-methoxyethoxymethoxyphenyl)-4-oxo-4H-quinoline-3-carboxylate By a procedure similar to that of Example 22 step 5, ethyl 2-(4-(3-acetamidopyrrolidin-1-yl)-3-(2-methoxyethoxymethoxyanilino)-2,3,5,6-tetrafluorobenzoyl)acrylate is cyclized and the title product is prepared.

Step 4. Ethyl 7-(3-acetamidopyrrolidin-1-yl)-5-benzylamino-6-fluoro-1-(2-methoxyethoxymethoxyphenyl)-4-oxo-4H-quinoline-3-carboxylate Ethyl 7-(3-acetamidopyrrolidin-1-yl)-5,6-difluoro-1-(2-methoxyethoxymethoxyphenyl)-4-oxo-4H-quinoline-3-carboxylate is reacted with benzylamine by a procedure similar to that of Example 22 step 3 to prepare the title compound.

Step 4. Ethyl 7-(3-acetamidopyrrolidin-1-yl)-5-acetamido-6-fluoro-1-(2-methoxyethoxymethoxyphenyl)-4-oxo-4H-quinoline-3-carboxylate The benzyl protecting group is removed by hydrogenolysis with hydrogen in the presence of a palladium catalyst, and the resulting amino group is reprotected with a acetyl protecting group by reaction with acetic anhydride in methanol at from 0° C. to 50° C.

Step 5. Ethyl 1-(3-acetamidopyrrolidin-1-yl)-3-acetamido-2-fluoro-4-oxo-4H-quino[2,3,4-i,j][1,4]benzoxazine-5-carboxylate Ethyl 7-(3-acetamidopyrrolidin-1-yl)-5-acetamido-6-fluoro-1-(2-methoxyethoxymethoxyphenyl)-4-oxo-4H-quinoline-3-carboxylate is deprotected at the phenolic position by selective hydrolysis with trifluoroacetic acid in methylene chloride to prepare ethyl 7-(3-acetamidopyrrolidin-1-yl)-5-acetamido-6-fluoro-1-(2-hydroxyphenyl)-4-oxo-4H-quinoline-3-carboxylate. This compound is then cyclized by a procedure similar to that of Example 22 step 5 to prepare the title compound.

Step 6. 3-amino-1-(3-aminopyrrolidin-1-yl)-2-fluoro-4-oxo-4H-quino[2,3,4-i,j][1,4]benzoxazine-5-carboxylic acid hydrochloride.

The protecting groups are removed from ethyl 1-(3-aminopyrrolidin-1-yl)-3-t-N-butyloxycarbonylamino-2-fluoro-4-oxo-4H-quino[2,3,4-i,j][1,4]benzoxazine-5-carboxylate by a procedure similar to that of Example 18 step 2 to prepare the title compound.

EXAMPLE 37

1-(3-Alanylalanylaminopyrrolidin-1-yl)-2-fluoro-4-oxo-4H-quino[2,3,4-i,j][1,4]benzoxazine-5-carboxylic acid hydrochloride Step 1. 1-(3-(t-butyloxycarbonylalanyl)aminopyrrolidin-1-yl)-2-fluoro-4-oxo-4-H-quino[2,3,4-i,j][1,4]benzoxazine-5-carboxylic acid A 3.01 g (7.2 mmol) sample of 1-(3-aminopyrrolidin-1-yl)-2-fluoro-4-oxo-4H-quino[2,3,4-i,j][1,4]benzoxazine-5-carboxylic acid hydrochloride (prepared as described in U.S. Pat. No. 4,607,032, which is incorporated herein by reference) was suspended in 150 mL of dry DMF and cooled at 0° C. for 15 min. To this suspension was added in one portion 2.27 g (7.92 mmol) of t-butyloxycarbonyl-L-alanine-N-hydroxysuccinimide and 1.60 g (15.8 mmol) of N-methylmorpholine. The mixture was cooled for another hour and the mixture stirred at room temperature until the reaction was complete. The resulting solution was poured into 700 mL of 0.5N HCl and the mixture was extracted with $CHCl_3$. The extract was washed with saturated NaCl solution, dried over anhydrous $MgSO_4$, and concentrated to leave a residue consisting of residual DMF and product. The DMF was removed by co-distillation with toluene to leave a yellow solid, which was triturated with ether, separated and dried at 60° C. under vacuum to afford 3.77 g of the title product. mp=202°–4° C. MS (DCl-$NH_3$) M/Z: 553 (M+H). 1H-NMR ($CDCl_3$) δ: 1.43 (m, 13H), 1.62 (m, 1H), 2.13 (m, 2H), 3.70 (m, 2H), 4.05 (m, 2H), 4.25 (m, 1H), 4.60 (m, 1H), 7.13 (m, 2H), 7.35 (m, 3H), 8.74 (m, 1H), 14.85 (m, 1H). Anal calc. for $C_{28}H_{29}FN_4O_7$: C, 60.86; H, 5.29; N, 9.95; found: C, 60.81; H, 5.24; N, 10.06.

Step 2. 1-(3-alanylaminopyrrolidin-1-yl)-2-fluoro-4-oxo-4H-quino[2,3,4-i,j][1,4]-benzoxazine-5-carboxylic acid hydrochloride A 2.79 g (5.05 mmol) sample of the compound from step 1 above was added to 100 mL of 1M HCl in acetic acid, and the suspension stirred at room temperature for 1.5 hours. The solvent was evaporated under vacuum to leave a solid residue, which was co-distilled with ethanol, then methanol, and dried under vacuum. The residue was washed with ether and dried under vacuum at 70° C. to afford 2.52 g (100% yield) of the title product. mp=211°–12° C. MS (DCl-$NH_3$) M/Z: 453 (M+H). 1H-NMR ($CD_3OD$) δ: 1.55 (m, 3H), 2.05 (m, 1H), 2.25 (m, 1H), 3.65 (m, 1H), 3.78 (m, 1H), 3.98 (m, 2H), 4.06 (m, 1H), 4.47 (m, 1H), 7.16 (m, 2H), 7.30 (m, 2H), 7.62 (m, 1H), 8.88 (m, 1H). IR (KBr): 1630, 1680, 1720 cm$^{-1}$. Anal calc. for $C_{23}H_{22}ClFN_4O_5 \cdot H_2O$: C, 54.49; H, 4.77; N, 11.05; found: C, 54.73; H, 4.61; N, 10.82.

Step 3. 1-(3-(t-butyloxycarbonylalanyl)alanylaminopyrrolidin-1-yl)-2-fluoro-4-oxo-4H-ouino[2,3,4-i,j][1,4]benzoxazine-5-carboxylic acid A 2.49 g (5.09 mmol) sample of the compound from step 2 above was suspended in 60 mL of dry DMF and cooled at 0° C. for 15 minutes. To this suspension was added in one portion 1.60 g (5.6 mmol) of t-butyloxycarbonyl-L-alanine-N-hydroxysuccinimide and 1.13 g (11.3 mmol) of N-methylmorpholine. The mixture was cooled for another hour, and then stirred at room temperature until the reaction was complete (16 hours). The reaction product was worked up as described in step 1 above to afford 2.47 g (78% yield) of the title product as a yellow solid. mp=193°–5° C. MS (DCl-$NH_3$) M/Z: 624 (M+H). 1H-NMR ($CDCl_3$) δ: 1.33 (m, 3H), 1.38 (m, 3H), 1.45 (m, 10H), 2.15 (m, 2H), 3.70 (m, 2H), 4.05 (m, 4H), 4.50 (m, 2H), 4.90 (m, 1H), 7.16 (m, 1H), 7.30 (m, 2H), 7.48 (m, 1H), 8.90 (m, 1H), 9.02 (m, 1H), 14.86 (m, 1H). Anal calc. for $C_{31}H_{34}FN_5O_8$: C, 59.70; H, 5.49; N, 11.23; found: C, 59.76; H, 5.10; N, 10.73. IR ($CDCl_3$) 1630, 1680, 1715 cm$^{-1}$.

Step 4. 1-(3-alanylalanylaminopyrrolidin-1-yl)-2-fluoro-4-oxo-4H-quino[2,3,4-i,j][1,4]benzoxazine-5-carboxylic acid hydrochloride A 2.43 g (3.9 mmol) sample of the compound from step 3 above was added to 100 mL of 1M HCl in acetic acid, and the suspension stirred at room temperature for 1.5 hours. The solvent was evaporated under vacuum to leave a solid residue, which was co-distilled with ethanol, then methanol, and dried under vacuum. The residue was washed with ether and dried under vacuum at 75° C. to afford 2.22 g (100% yield) of the title product. mp=200° C., dec. MS (DCl-$NH_3$) M/Z: 524 (M+H).

EXAMPLE 38

1-(3-Norvalylnorvalylaminopyrrolidin-1-yl)-2-fluoro-4-oxo-4H-quino[2,3,4-i,j][1,4]benzoxazine-5-carboxylic acid hydrochloride Step 1. 1-(3-(t-Butoxycarbonyl)norvalylnorvalylaminopyrrolidin-1-yl)-2-fluoro-4-oxo-4H-quino[2,3,4-i,j][1,4]benzoxazine-5-carboxylic acid A 2.24 g (4.33 mmol) sample of 1-(3-norvalylaminopyrrolidin-1-yl)-2-fluoro-4-oxo-4H-quino[2,3,4-i,j][1,4]benzoxazine-5-carboxylic acid, prepared as described in Example 8, was suspended in 60 mL of dry DMF and cooled at 0° C. for 15 minutes. To this suspension was added in one portion 1.50 g (4.77 mmol) of t-butyloxycarbonyl-L-norvaline-N-hydroxysuccinimide and 0.964 g (9.53 mmol) of N-methylmorpholine. The mixture was cooled for another hour, the mixture was stirred at room temperature until the reaction was complete (16 hours). The reaction product was worked up as described in Example 37 step 1 above to afford 1.59 g (54% yield) of the title product as a yellow solid. mp=240°–243° C. MS (DCl-$NH_3$) M/Z: 680 (M+H). 1H-NMR (DMSO) δ: 0.80 (m, 6H), 1.32 (m, 13H), 1.50 (m, 4H), 1.84 (m, 1H), 2.10 (m, 1H), 3.47 (m, 2H), 3.90 (m, 2H), 4.25 (m, 2H), 6.91 (m, 1H), 7.23 (m, 2H), 7.34 (m, 1H), 7.46 (m, 1H), 7.73 (m, 2H), 7.97 (m, 1H), 8.24 (m, 1H), 9.08 (m, 1H). Anal calc. for $C_{35}H_{42}FN_5O_8 \cdot 1.5H_2O$: C, 59.47; H, 6.42; N, 9.91; found: C, 59.28; H, 6.23; N, 10.14. IR (KBr): 1630, 1690, 1710 cm$^{-1}$.

Step 2. 1-(3-norvalylnorvalylaminopyrrolidin-1-yl)-2-fluoro-4-oxo-4H-quino[2,3,4-i,j][1,4]benzoxazine-5-carboxylic acid hydrochloride By a procedure similar to that of Example 37 step 4, the BOC-protecting group was removed from a 1.56 g (2.29 mmol) sample of the compound from step 1 above to afford 1.35 g of the title product. mp=223°–6° C. MS (DCl-$NH_3$) M/Z: 580 (M+H). 1H-NMR ($CD_3OD$) δ: 0.95 (m, 6H), 1.42 (m, 4H), 1.80 (m, 4H), 2.00 (m, 2H), 2.23 (m, 2H), 3.60 (m, 1H), 3.77 (m, 1H), 3.95 (m, 3H), 4.40(m, 2H), 7.20 (m, 2H), 7.32 (m, 2H), 7.70 (m, 1H), 9.00 (m, 1H). IR (KBr): 1630, 1660, 1720 cm$^{-1}$.

EXAMPLE 39

1-(3-Alanylnorvalylaminopyrrolidin-1-yl)-2-fluoro-4-oxo-4H-quino[2,3,4-i,j][1,4benzoxazine-5-carboxylic acid hydrochloride Step 1. 1-(3-(t-Butoxycarbonyl)alanylnorvalylaminopyrrolidin-1-yl)-2-fluoro-4-oxo-4H-quino[2,3,4-i,j][1,4]benzoxazine-5-carboxylic acid A 1.51 g (2.92 mmol) sample of 1-(3-norvalylaminopyrrolidin-1-yl)-2-fluoro-4-oxo-4H-quino[2, 3,4-i,j][1,4]benzoxazine-5-carboxylic acid hydrochloride, prepared as described in Example 8, was suspended in 60 mL of dry DMF and cooled at 0° C. for 15 minutes. To this suspension was added in one portion 0.920 g (3.21 mmol) of t-butyloxycarbonyl-L-alanine-N-hydroxysuccinimide and 0.650 g (6.42 mmol) of N-methylmorpholine. The mixture was cooled for another hour, and the mixture stirred at room temperature until the reaction was complete (16 hours). The reaction product was worked up as described in Example 37 step 1 to afford 1.65 g (87% yield) of the title product as a yellow solid. mp=240°–2° C. MS (DCl-NH$_3$) M/Z: 652 (M+H). 1H-NMR (CDCl$_3$) δ: 0.92 (m, 3H), 1.23 (m, 2H), 1.43 (m, 12H), 1.55 (m, 3H), 1.68 (m, 2H), 4.05 (m, 2H), 4.42 (m, 1H), 4.55 (m, 1H), 4.87 (m, 1H), 6.60 (m, 1H), 7.15 (m, 2H), 7.45 (m, 1H), 8.89 (m, 1H), 14.8 (m, 1H). IR (CHCl$_3$): 1630, 1690, 1710 cm$^{-1}$. Anal calc. for C$_{33}$H$_{38}$FN$_5$O$_8$; C, 60.82; H, 5.88; N, 10.75; found: C, 60.46; H, 5.72; N, 10.65.

Step 2. 1-(3-Alanylnorvalylaminopyrrolidin-1-yl)-2-fluoro-4-oxo-4H-quino[2,3,4-i,j][1,4]benzoxazine-5-carboxylic acid hydrochloride By a procedure similar to that of Example 37 step 4, the BOC-protecting group was removed from a 1.61 g (2.47 mmol) sample of the compound from step 1 above to afford 1.42 g of the title product. mp=200°–2° C. MS (DCl-NH$_3$) M/Z: 552 (M+H). IR (KBr): 1630, 1660, 1715 cm$^{-1}$. 1H-NMR (CD$_3$OD) δ: 0.96 (m, 3H), 1.50 (m, 5H), 1.73 (m, 2H), 2.02 (m, 1H), 2.22 (m, 1H), 3.61 (m, 1H), 2.76 (m, 1H), 4.00 (m, 3H), 4.41 (m, 2H), 7.14 (m, 2H), 7.30 (m, 2H), 7.62 (m, 1H), 8.89 (m, 1H). Anal calc. for C$_{28}$H$_{31}$ClFN$_5$O$_6$•½ H$_2$O: C, 57.19; H, 5.31; N, 11.91; found: C, 56.85; H, 5.47; N, 11.77.

EXAMPLE 40

1-(3-Norvalylalanylaminopyrrolidin-1-yl)-2-fluoro-4-oxo-4H-quino[2,3,4-i,j][1,4]benzoxazine-5-carboxylic acid hydrochloride Step 1. 1-(3-t-Butoxycarbonylnorvalylalanylaminopyrrolidin-1-yl)-2-fluoro-4-oxo-4H-quino[2,3,4-i,j][1,4]benzoxazine-5-carboxylic acid A 0.904 g (1.85 mmol) sample of 1-(3-alanylaminopyrrolidin-1-yl)-2-fluoro-4-oxo-4H-quino[2,3,4-i,j][1,4]benzoxazine-5-carboxylic acid, from Example 37 step 2 above, was reacted with t-butyloxycarbonyl-L-norvaline-N-hydroxysuccinimide in a procedure similar to that of Example 38 to afford 1.05 g of the title product. mp=238°–241° C. MS (DCl-NH$_3$) M/Z: 652 (M+H). 1H-NMR (DMSO) δ: 0.83 (m, 3H), 1.21 (m, 3H), 1.35 (m, 10H), 1.50 (m, 2H), 1.86 (m, 1H), 2.12 (m, 1H), 3.50 (m, 1H), 3.76 (m, 1H), 3.85 (m, 2H), 2.95 (m, 2H), 4.28 (m, 2H), 6.87 (m, 1H), 7.25 (m, 2H), 7.35 (m, 1H), 7.46 (m, 1H), 7.80 (m, 1H), 7.98 (m, 1H), 8.15 (m, 1H), 9.08 (m, 1H), 14.87 (m, 1H). IR (KBr): 1630, 1685, 1715 cm$^{-1}$. Anal calc. for C$_{33}$H38FN$_5$O$_8$: C, 60.82; H, 5.88; N, 10.75; found: C, 60.73; H, 5.90; N, 10.70.

Step 2. 1-(3-Norvalylalanylaminopyrrolidin-1-yl)-2-fluoro-4-oxo-4H-quino[2,3,4-i,j][1,4]benzoxazine-5-carboxylic acid hydrochloride By a procedure similar to that of Example 37, Step 4, the BOC-protecting group was removed from a 1.00 g (1.54 mmol) sample of the compound from step 1 above to afford 0.873 g of the title product. mp=238°–40° C. MS (DCl-NH$_3$) M/Z: 552 (M+H). 1H-NMR (CD$_3$OD) δ: 0.95 (m, 3H), 1.25 (m, 1H), 1.42 (m, 5H), 1.83 (m, 2H), 2.02 (m, 1H), 2.25 (m, 1H), 3.52 (m, 1H), 3.83 (m, 2H), 3.98 (m, 1H), 4.06 (m, 1H), 4.45 (m, 1H), 7.22 (m, 2H), 7.33 (m, 1H), 7.45 (m, 1H), 7.75 (m, 1H), 8.88 (m, 1H). IR (KBr): 1630, 1660, 1720 cm$^{-1}$. Anal calc. for C$_{28}$H$_{31}$ClFN$_5$O$_6$•½ H$_2$O: C, 56.31; H, 5.40; N, 11.73; found: C, 56.33; H, 5.27; N, 11.54.

EXAMPLE 41

Assay of In Vitro Cytotoxicity

The in vitro activity of the compounds of the present invention was demonstrated using a three day microtiter assay to measure the metabolic activity of cultured cells exposed to a range of cytotoxic drug concentrations. Metabolic activity was measured by the cells' ability to reduce the tetrazolium dye, 3-(4,5-dimethylthiazol-2-yl)-2,5-diphenyltetrazolium bromide (MTT), to a quantifiable colored formasan derivative. Surviving cells reduce the MTT dye. The inhibitory concentrations of killing 50% of the cells (IC$_{50}$s) were calculated. Testing was in accord with the following protocol:

Test compounds and a reference antineoplastic agent, ADRIAMYCIN (doxorubicin hydrochloride), were dissolved in dimethyl sulfoxide (DMSO) and diluted, first with Earle's Balanced Salt Solution, followed by culture medium, to twice the highest concentration of the compound to be tested. From this concentrated stock, two-fold serial dilutions were prepared in 96-well microtiter trays, each well containing twice the desired final concentration of the compound. Each concentration was tested in triplicate and compared to triplicate drug-free controls.

The cells were grown in the same medium used for diluting the compounds. Adherent cells were harvested by trypsinization according to the following procedure:

1. Removing the medium by aspiration.
2. Rinsing the cell monolayer twice with Earle's Balanced Salt Solution.
3. Adding trypsin (0.05%)/EDTA (0.53 mM), using approximately 0.2 mL of solution for each 25 cm$^2$; tilting to cover the monolayer, then withdrawing trypsin leaving only a thin film of solution; incubating at room temperature until cell monolayers detach.
4. When the cells have detached as determined by visual and/or microscopic observation, adding medium containing fetal calf serum to stop the action of the trypsin and resuspend the cells; triturating to aid dissociation of cell clumps.
5. Determining the number of cells per milliliter by electronic cell counter (e.g. Coulter Counter) or by mixing an aliquot of cell suspension with Trypan Blue (0.4% in normal saline) and counting the viable cells using a hemacytometer.

After harvesting by trypsinization, viable cell counts were determined and cell density was adjusted to 25,000 cells/mL. Inoculum (0.1 mL) was then added to each well for a final concentration of 2,500 cells per well. Addition of the inoculum was used to dilute the test compounds to the desired concentration.

Microtiter trays were incubated for three days at 36° C. in a humidified atmosphere containing 5% carbon dioxide.

After three days, 20 microliters of 5 mg/mL MTT in phosphate-buffered solution were added to each well of the microtiter trays. The microtiter trays were then returned to the incubator for two to four hours to allow the surviving cells to reduce the dye. After this incubation, both the medium and the unreduced dye were removed by aspiration. DMSO was added to each well to dissolve the water-insoluble, colored end product of the dye reduction for spectrophotometric measurement at 570 nm.

The results obtained which clearly show the cytotoxicity of the compounds of Examples 5, 6, 7 and 8 against human and human tumor cell lines A549, HCT-8, HT-29 and P388-D1, are illustrated in Table 1. (A549 is a human lung cancer cell line; HCT-8 is a human colon cancer cell line; HT-29 is a human colon cancer cell line; and P388-D1 is a mouse leukemia cell line.)

TABLE 1

| Compound[a] | In Vitro Cytotoxicity ($IC_{50}$) Against Selected Tumor Cell Lines | | | |
|---|---|---|---|---|
| | A549 | HCT-8 | HT-29 | P388-D1 |
| 8 | 0.512 | 0.075 | — | <0.05 |
| ADR[b] | 0.052 | 0.038 | — | 0.016 |
| 5 | 0.13 | — | 0.078 | 0.011 |
| 6, step 2 | 1.01 | — | 0.64 | 0.65 |
| ADR | 0.049 | — | 0.031 | 0.016 |
| 6 | 0.13 | — | 0.049 | 0.067 |
| 7 | 4.1 | — | 0.21 | 0.11 |
| ADR | 0.14 | — | 0.091 | 0.010 |

Note:
a = Compound numbers correspond to those of Examples, the title compounds of which were tested.
b = ADR represents ADRIAMYCIN (doxorubicin hydrochloride)

Compounds from Examples 4, 6, 8, 9 and 10 were additionally tested against human and murine tumor cell lines A549, HT-29, P388-D1, P388, P388-ADR(0.0), P388-ADR(0.1) and B16F109. (P388 is a mouse leukemia cell line similar to P388-D1, but animal-passaged; P388-ADR (0.0) is an ADRIAMYCIN-resistant variant of P388, the inoculum of which is grown in drug-free medium; P388-ADR (0.1) is an ADRIAMYCIN-resistant variant of P388, the inoculum of which is grown in medium with 0.1 mcg.ml ADRIAMYCIN; and B16F10 is a mouse melanoma.) The results are presented in Table 2; as shown in the table, the compounds of the present invention are effective cytotoxic agents even against the ADRIAMYCIN-resistant cell line P388-ADR.

EXAMPLE 42

In Vivo Antitumor Activiity

The in vive antitumor activities of the compound of Example 8 and 1-(3-aminopyrrolidin-1-yl)-2-fluoro-4-oxo-4H-[2,3,4-i,j][1,4]benzoxazine-5-carboxylic acid (prepared as described in U.S. Pat. No. 4,607,032) were demonstrated using the ascitic leukemia tumor line P388. Prior to testing, P388 was propagated intraperitoneally in female DBA2 mice. The ascitic tumors were intraperitoneally injected in female $B_6D_2F_1$ mice at a concentration of $10^6$ cells per mouse. The mice were treated with antitumor agents administered once daily for five consecutive days, with the antineoplastic 5-fluorouracil used as a positive control.

All drugs were administered intraperitoneally in 5% aqueous dextrose or other suitable diluent. Drug efficacy was evaluated based on prolongation of mean survival time (MST). Improvement of MST was calculated as % MST(T/C), the percent ratio of mean survival times of test (T) versus control (C) mice. Compounds having % MST(T/C) values greater than 125 are considered to have significant activity. The antitumor activity of the two compounds in the P388 systemic leukemia model is illustrated in Table 3 below.

TABLE 3

| In Vivo Activity Against Systemic Tumor P388. | | |
|---|---|---|
| Compound | Dose (mg/kg) | % MST(T/C) |
| A | 50 | 180 |
| " | 25 | 170 |
| " | 12.5 | 165 |
| " | 6.25 | 160 |
| 5-Fluorouracil | 20 | 160 |
| 8 | 31.25 | 63.6 |
| " | 15.62 | 209.1 |
| " | 7.81 | 200.0 |

TABLE 2

| Compound | In Vitro Cytoxicity ($IC_{50}$) Against Additional Tumor Cell Lines | | | | | | |
|---|---|---|---|---|---|---|---|
| | A549 | HT-29 | P388-D1 | P388 | P388-ADR(0.0) | P388-ADR(0.1) | B16F10 |
| ADR[a] | 0.313 | 0.285 | 0.025* | 0.0022 | 2.59 | 1.9* | 0.005 |
| A[b] | 0.26 | 0.10 | — | 0.019 | 0.12 | — | 0.021 |
| 4 | 0.122 | 0.0431 | — | 0.0384 | 0.240 | — | 0.0221 |
| 6 | 0.23 | 0.076 | 0.080 | 0.071 | 0.20 | 0.20 | 0.056 |
| 7 | 4.1 | 0.20 | 0.11 | | | | |
| 8 | 0.591 | 0.195 | — | 0.0395 | 0.394 | — | 0.0271 |
| 9 | 0.23 | 0.075 | 0.081 | 0.062 | 0.19 | 0.18 | 0.048 |
| 10 | 0.187 | 0.0875 | — | 0.108 | 0.447 | — | 0.0573 |
| 15 | 0.034 | 0.015 | | 0.012 | | | 0.015 |
| 16 | 0.23 | 0.055 | | 0.017 | 0.12 | | 0.018 |
| 17 | 0.042 | 0.068 | | 0.021 | 0.10 | | 0.011 |
| 18 | 0.11 | 0.040 | | 0.047 | 0.13 | | 0.024 |
| 19 | 0.24 | 0.052 | | 0.047 | .016 | | 0.049 |
| 21 | 0.247 | 0.078 | | 0.063 | | | 0.045 |
| 29 | 6.0 | 1.4 | | 0.54 | 49.4 | | 0.56 |
| 30 | 4.1 | 1.6 | | 0.60 | | | 1.3 |
| 32 | 0.134 | 0.042 | | 0.022 | | | 0.018 |
| 35 | 0.26 | 0.093 | | 0.034 | | | 0.077 |

NOTES:
a = Data for ADRIAMYCIN (doxorubicin hydrochloride) are averages from two tests, except for data marked with an asterisk (*), which are single-test data.
b = Compound A is 1-(3-aminopyrrolidin-1-yl)-2-fluoro-4-oxo-4H-[2,3,4-i,j][1,4]-benzoxazine-5-carboxylic acid (from U.S. Pat. No. 4,607,032, Example 5).

TABLE 3-continued

In Vivo Activity Against Systemic Tumor P388.

| Compound | Dose (mg/kg) | % MST(T/C) |
|---|---|---|
| " | 3.9 | 177.3 |
| 5-Fluorouracil | 20 | 186.67 |

Compound A and the compound of Example 8 were also tested against solid tumors, namely Lewis lung carcinoma on the one hand and C-26 colon adenocarcinoma and M5076 ovadan sarcoma on the other. Lewis lung carcinoma was inoculated subcutaneously to flanks of mice on day 0. The compound being tested (Compound A) was administered intraperitoneally (IP) from day 1 to day 9 for a total of nine injections. Tumor weights were measured on day 14 and drug efficacy assessed based on reduction of mean tumor mass (MTM), expressed as the percent ratio of treated (T) to control (C) MTM's. Compounds having % MTM(T/C) values of less than or equal to 40 are considered to have significant activity. These values are shown below in Table 4.

In the case of C-26 colon adenocarcinema, the tumor was implanted IP into mice on day 0. The compound to be tested (the compound of Example 8) was administered IP at days 1, 5, and 9 and the results recorded on day 60. % MST(T/C) values were calculated as before and are shown below for two separate trials.

For M5076 ovarian sarcoma, the solid tumor was implanted subcutaneously into mice on day 0. The compound to be tested (the compound of Example 8) was administered IP every 2 days up to day 11, starting on day 1. Both % MST(T/C) and % MTM(T/C) values were calculated, and are presented below.

TABLE 4

In Vivo Activity Against Solid Tumors.

| Compound | Dose | Lewis Lung % MTM(T/C) | C-26 % MST(T/C) | M5706 % MST(T/C) | M5706 % MTM(T/C) |
|---|---|---|---|---|---|
| A | 50 | 0.41 | — | — | — |
| " | 25 | 0.47 | — | — | — |
| " | 12.5 | 0.67 | — | — | — |
| " | 6.25 | 0.68 | — | — | — |
| 8 | 40 | — | 52.3; 43.9 | 39.1 | — |
| " | 20 | — | 141.6; 169.3 | 138.1 | 0.22 |
| " | 10 | — | 134.0; 157.9 | 154.4 | 0.49 |
| " | 5 | — | 115.2; 140.6 | 148.4 | 0.62 |

The results shown above demonstrate the in vivo efficacy of compounds of the invention in prolonging survival time and reducing tumor mass in subjects inoculated with a variety of neoplasms.

EXAMPLE 43

Aqueous Solubility of Selected Compounds

The effect of peptidyl substitution on the solubility of the compounds of the invention was examined by dissolving samples thereof in water. The results, shown in Table 5 below, demonstate the greatly increased solubility resulting from the formation of peptidyl derivatives of the parent compounds.

TABLE 5

| Compound | Solubility in water (mg/ml) |
|---|---|
| 37 | 28.15 |
| 38 | 11.05 |
| 40 | >47.8 |
| 8 | 10.7 |
| A | 8.8 |

EXAMPLE 44

In Vivo Antitumor Activity

The title compound of Example 37 above was tested against solid tumors in mice, using 1,3-bis(2-chloroethyl)-1-nitrosourea (BCNU) as a positive control. The tumor lines were M5076, an ovarian sarcoma implanted intraperitoneally (IP), and C-26, a colon adenocarcinoma, implanted intraperitoneally (IP) and subcutaneously (SC) in separate trials.

All drugs were administered in 5% aqueous dextrose or other suitable diluent. Drug efficacy was determined by prolonged survival times of the test animals or reduced tumor mass as compared to negative controls. Test groups consisted of 10 mice. Control groups consisted of 20 mice. Animals were of one sex and of similar weight. Prior to testing, the tumor cell lines were propagated in BALB/cj mice. Tumor implants were aliquots of a donor pool brei.

In the IP trials, the mean survival time (MST) of the groups of mice was determined, not counting animals surviving at the conclusion of the trial, and the mean lifespan comparison value of % MST(T/C) calculated, which value represents the ratio of treated to control group MST's expressed as a percentage. Compounds having % MST(T/C) values greater than 125 were considered to demonstrate significant activity.

For M5076 ovarian sarcoma, the tumor was implanted IP into $BDF_1$ mice on day 0. The test compound was administered four times a day IP from day 1 to day 9 for a total of nine days. The activity of the test compound is illustrated in Table 6 below, which shows a significant improvement in survival time in animals treated with the compound of Example 37.

For C-26 colon adenocarcinoma, the tumor was implanted into $CD_2F_1$ mice, IP and SC in separate trials. For the C-26 IP trial, the tumor was implanted IP on day 0. The test compound were administered four times a day IP from day 1 to day 9 for a total of nine days. BCNU was administered four times a day on days 1, 5 and 9. The antitumor activities of the test compound and BCNU for C-26 IP are shown in Table 7 below. Again, a significant improvement in survival time in animals treated with the compound of Example 37 is demonstrated.

For the C-26 SC trial, the tumor was implanted SC into mice on day 0. The test compound was administered four times a day IP from day 1 to day 9 for a total of nine days. BCNU was administered four times a day on days 1, 5, and 9. The mean tumor masses were determined on day 11 and day 21, and the experiment terminated on day 60. The mean tumor mass (MTM) inhibition value of % MTM(T/C) was calculated, which value represents the ratio of treated to control group MTM's expressed as a percentage. The anti-tumor activities of the compound of Example 37 and BCNU for C-26 SC are reported in Table 8 below. Compounds having % MTM(T/C) values of less than 40 are considered to possess moderate activity and % MTM(T/C) values of less than 10 are considered to demonstrate significant activity. The results for both days 11 and 21 show that the compound of Example 37 is significantly active against this tumor cell line when implanted subcutaneously.

TABLE 6

In Vivo Activity Against M5076 Implanted Intraperitoneally

| Treatment | Dose (mg/kg) | MST | % MST(T/C) |
|---|---|---|---|
| 37 | 100 | 3.2 | 15[a] |
| " | 50 | 4.4 | 21[a] |
| " | 25 | 9.3 | 45[a] |
| " | 12.5 | 44.6[b] | 215 |
| None | — | 20.7 | (100) |

Notes:
[a]Toxicity due to the test compound noted.
[b]One of ten test animals survived the trial.

TABLE 7

In Vivo Activity Against C-26 Implanted Intraperitoneally

| Treatment | Dose (mg/kg) | MST | % MST(T/C) |
|---|---|---|---|
| 37 | 20 | 40.7[a] | 197 |
| " | 10 | 40.2 | 195 |
| " | 5 | 36.0 | 174 |
| " | 2.5 | 30.3 | 147 |
| BCNU | 10 | 41.4[b] | 201 |
| None | — | 20.7 | (100) |

Notes:
[a]Three of ten test animals survived the trial.
[b]One of ten test animals survived the trial.

TABLE 8

In Vivo Activity Against C-26 Implanted Subcutaneously

| Day | Treatment | Dose (mg/kg) | MTM (mg) | % MTM(T/C) |
|---|---|---|---|---|
| 11 | 37 | 20 | 0 | 0 |
| " | " | 10 | 74 | 24 |
| " | " | 5 | 205 | 66 |
| " | " | 2.5 | 302 | 97 |
| " | BCNU | 10 | 2 | 1 |
| " | None | — | 312 | (100) |
| 21 | 37 | 20 | 169 | 5 |
| " | " | 10 | 1336 | 41 |
| " | " | 5 | 2462 | 75 |
| " | " | 2.5 | 2617 | 79 |
| " | BCNU | 10 | 244 | 7 |
| " | None | — | 3295 | (100) |

It is understood that the foregoing detailed description and accompanying examples am merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A method of inhibiting the growth of neoplastic cells comprising exposing the cells to an effective amount of a compound of the formula

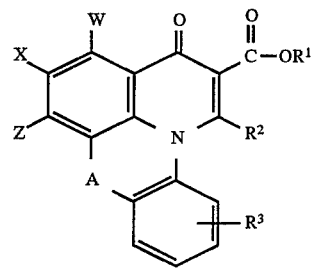

or a pharmaceutically acceptable salt, ester, or amide thereof, in which

A is a sulfur atom;

$R^1$ is hydrogen;

$R^2$ is selected from the group consisting of (a) hydrogen, (b) alkyl of from 1 to 6 carbon atoms, (c) alkoxy of from 1 to 6 carbon atoms, and (d) sulfhydroalkyl of from 1 to 6 carbon atoms;

$R^3$ is one or more groups independently selected from the group consisting of (a) hydrogen, (b) halogen, (c) nitro, (d) alkyl of from 1 to 6 carbon atoms, (e) carboxyl, (f) methylenedioxy, (g) cyano, (h) halo-substituted alkyl of from 1 to 6 carbon atoms, (i) hydroxy-substituted alkyl of from 1 to 6 carbon atoms, (j) a group of the formula —$YR^4$ in which Y is O or S, and $R^4$ is hydrogen or alkyl of from 1 to 6 carbon atoms, and (k) an amine of the formula —$NR^5R^6$ where $R^5$ and $R^6$ are independently selected from hydrogen and alkyl of from 1 to 6 carbon atoms, W is selected from the group consisting of (a) hydrogen, (b) alkyl of from 1 to 6 carbon atoms, (c) amino, (d) halogen, (e) alkoxy, (f) hydroxyl, (g) alkylamino, and (h) halo-substituted alkyl;

X is selected from the group consisting of (a) hydrogen, (b) halogen, (c) alkyl of from 1 to 6 carbon atoms and, (d) halo-substituted alkyl of from 1 to 6 carbon atoms; and Z is selected from the group consisting of
(a) halogen,
(b) a nitrogen-containing heterocycle of the formula

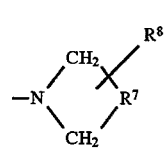

where (i) $R^7$ is selected from —$CH_2$—, —$CH_2CH_2$—, —$CH_2CH_2CH_2$—, —$CH_2CH_2NHCH_2$—, and a group of the formula —CH$_2$R$^9$CH$_2$— where R$^9$ is selected from S, O, and NH, and (ii) R$^8$ is 1 or 2 groups independently selected from the group consisting of hydrogen, alkyl of from 1 to 6 carbon atoms, halo-substituted alkyl of from 1 to 6 carbon atoms, amino-substituted alkyl of from 1 to 6 carbon atoms, hydroxy-substituted alkyl of from 1 to 6 carbon atoms, alkylaminoalkyl wherein each alkyl portion contains from 1 to 6 carbon atoms, hydroxy, alkanoyl of from 1 to 6 carbon atoms, spirocycloalkyl group of from 5 to 10 carbon atoms, and an amine of the formula —NR$^{10}$R$^{11}$ where R$^{10}$ and R$^{11}$ are independently selected from hydrogen, acetyl, alkyl of from 1 to 6 carbon atoms, an α-amino acid and a dipeptide group joined to the nitrogen with an amide linkage, or one of R$^{10}$ and R$^{11}$ is hydrogen and the other is selected from an alkanoyl group of from 1 to 6 carbon atoms, an α-amino acid and a dipeptide group joined to the nitrogen atom with an amide linkage; and (c) an amino group of the formula —NR$^{12}$R$^{13}$ where R$^{12}$ is selected from hydrogen and alkyl of from 1 to 10 carbon atoms, and where R$^{13}$ is selected from alkyl of from 1 to 10 carbon atoms, hydroxy-substituted alkyl of from 1 to 10 carbon atoms, an amino group, alkylamino of 1 to 6 carbon atoms, and dialkylamino of 1 to 6 carbon atoms;

or, taken together with the atoms to which they are attached, X and Z form —OCH$_2$O— or —OCH$_2$CH$_2$O—.

2. The method according to claim 1 wherein Z is selected from the group consisting of aminopyrrolidinyl, 2-methyl-4-aminopyrrolidinyl, norvalylaminopyrrolidinyl, alanylaminopyrrolidinyl, alanylalanylaminopyrrolidinyl, norvalylnorvalylaminopyrrolidinyl, alanylnorvalylaminopyrrolidinyl and norvalylalanylaminopyrrolidinyl.

3. The method of claim 1 wherein the neoplastic cells are selected from the group consisting of systemic leukemia, lewis lung carcinoma, colon adenocarcinoma, and ovarian sarcoma.

4. A compound having the formula

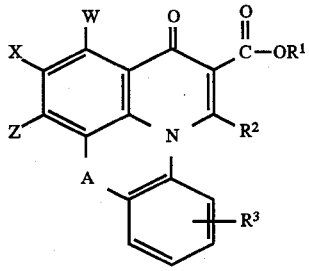

or a pharmaceutically acceptable salt, ester, or amide thereof, in which

A is a sulfur atom;

R$^1$ is hydrogen;

R$^2$ is selected from the group consisting of (a) hydrogen, (b) alkyl of from 1 to 6 carbon atoms, (c) alkoxy of from 1 to 6 carbon atoms, and (d) sulfhydroalkyl of from 1 to 6 carbon atoms;

R$^3$ is one or more groups independently selected from the group consisting of (a) hydrogen, (b) halogen, (c) nitro, (d) alkyl of from 1 to 6 carbon atoms, (e) carboxyl, (f) methylenedioxy, (g) cyano, (h) halo-substituted alkyl of from 1 to 6 carbon atoms, (i) hydroxy-substituted alkyl of from 1 to 6 carbon atoms, (j) a group of the formula —YR$^4$ in which Y is O or S, and R$^4$ is hydrogen or alkyl of from 1 to 6 carbon atoms, and (k) an amine of the formula —NR$^5$R$^6$ where R$^5$ and R$^6$ are independently selected from hydrogen and alkyl of from 1 to 6 carbon atoms, W is selected from the group consisting of (a) hydrogen, (b) alkyl of from 1 to 6 carbon atoms, (c) amino, (d) halogen, (e) alkoxy, (f) hydroxyl, (g) alkylamino, and (h) halo-substituted alkyl;

X is selected from the group consisting of (a) hydrogen, (b) halogen, (c) alkyl of from 1 to 6 carbon atoms and, (d) halo-substituted alkyl of from 1 to 6 carbon atoms; and Z is a nitrogen-containing heterocycle of the formula

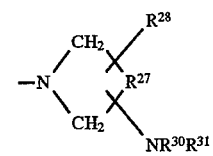

where (i) R$^{27}$ is selected from —CH$_2$—, —CH$_2$—CH$_2$—, and —CH$_2$—CH$_2$—CH$_2$—, (ii) R$^{28}$ is selected from hydrogen, halogen, alkyl of from 1 to 6 carbon atoms, halo-substituted alkyl of from 1 to 6 carbon atoms, and spirocycloalkyl of from 5 to 10 carbon atoms, and (iii) one of R$^{30}$ and R$^{31}$ is hydrogen and the other is selected from the group consisting of acetyl, α-amino acid and dipeptidyl;

or, taken together with the atoms to which they are attached, X and Z form —OCH$_2$CH$_2$O— or —OCH$_2$O—, with the proviso that R$^2$ is not hydrogen.

5. The compound according to claim 4 wherein Z is selected from the group consisting of norvalylaminopyrrolidinyl, alanylaminopyrrolidinyl, alanylalanylaminopyrrolidinyl, norvalylnorvalylaminopyrrolidinyl, alanylnorvalylaminopyrrolidinyl and norvalylalanylaminopyrrolidinyl.

6. A pharmaceutical composition having antineoplastic activity comprising a pharmaceutically acceptable carrier and a therapeutically effective amount of a compound as defined in claim 4.

7. The method according to claim 1 wherein the compound is selected from the group consisting of:

1-(3-aminopyrrolidin-1-yl)-2-fluoro-4-oxo-4H-quino[2,3,4-i,j][1,4]benzothiazine-5-carboxylic acid;

1-(3-norvalylaminopyrrolidin-1-yl)-2-fluoro-4-oxo-4H-quino[2,3,4-i,j][1,4]benzothiazine-5-carboxylic acid;

1-(3-alanylaminopyrrolidin-1-yl)-2-fluoro-4-oxo-4H-quino[2,3,4-i,j][1,4]benzothiazine-5-carboxylic acid;

1-(3-acetamidopyrrolidin-1-yl)-2-fluoro-9-nitro-4-oxo-4H-quino[2,3,4-i,j][1,4]benzothiazine-5-carboxylic acid;

1-(3-aminopyrrolidin-1-yl)-2,9-difluoro-4-oxo-4H-quino[2,3,4-i,j][1,4]benzothiazine-5-carboxylic acid;

1-(3-aminopyrrolidin-1-yl)-2-fluoro-9-methyl-4-oxo-4H-quino[2,3,4-i,j][1,4]benzothiazine-5-carboxylic acid;

1-(3-norvalylaminopyrrolidin-1-yl)-2-fluoro-9-methyl-4-oxo-4H-quino[2,3,4-i,j][1,4]benzothiazine-5-carboxylic acid;

1-(3-alanylaminopyrrolidin-1-yl)-2-fluoro-9-methyl-4-oxo-4H-quino[2,3,4-i,j][1,4]benzothiazine-5-carboxylic acid;

1-(3-aminopyrrolidin-1-yl)-2-fluoro-8-methyl-4-oxo-4H-quin[2,3,4-i,j][1,4]benzothiazine-5-carboxylic acid;

1-(3-norvalylaminopyrrolidin-1-yl)-2-fluoro-8-methyl-4-oxo-4H-quin[2,3,4-i,j][1,4]benzothiazine-5-carboxylic acid;

1-(3-alanylaminopyrrolidin-1-yl)-2-fluoro-8-methyl-4-oxo-4H-quin[2,3,4i,j][1,4]benzothiazine-5-carboxylic acid.

8. A compound according to claim 4 selected from the group consisting of:

1-(3-aminopyrrolidin-1-yl)-2-fluoro-4-oxo-4H-quino[2,3,4-i,j][1,4]benzothiazine-5-carboxylic acid;

1-(3-norvalylaminopyrrolidin-1-yl)-2-fluoro-4-oxo-4H-quino[2,3,4-i,j][1,4]benzothiazine-5-carboxylic acid;

1-(3-alanylaminopyrrolidin-1-yl)-2-fluoro-4-oxo-4H-quino[2,3,4-i,j][1,4]benzothiazine-5-carboxylic acid;

1-(3-acetamidopyrrolidin-1-yl)-2-fluoro-9-nitro-4-oxo-4H-quino[2,3,4-i,j][1,4]benzothiazine-5-carboxylic acid;

1-(3-aminopyrrolidin-1-yl)-2-fluoro-9-methyl-4-oxo-4H-quino[2,3,4-i,j][1,4]benzothiazine-5-carboxylic acid;

1-(3-alanylaminopyrrolidin-1-yl)-2-fluoro-9-methyl-4-oxo-4H-quino[2,3,4-i,j][1,4]benzothiazine-5-carboxylic acid;

1-(3-norvalylaminopyrrolidin-1-yl)-2-fluoro-8-methyl-4-oxo-4H-quin[2,3,4-i,j][1,4]benzothiazine-5-carboxylic acid;

1-(3-alanylaminopyrrolidin-1-yl)-2-fluoro-8-methyl-4-oxo-4H-quin[2,3,4-i,j][1,4]benzothiazine-5-carboxylic acid; and 1-(3-aminopyrrolidin-1-yl)-2-fluoro-8-methyl-4-oxo-4H-quin[2,3,4-i,j][1,4]benzothiazine-5-carboxylic acid.

9. An intermediate compound having the formula

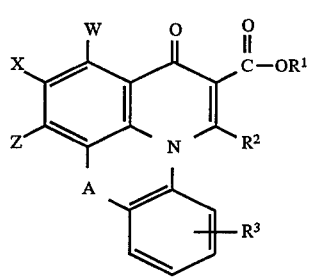

or a pharmaceutically acceptable salt, ester, or amide thereof, in which

A is a sulfur atom;

$R^1$ is a carboxy-protecting group;

$R^2$ is selected from the group consisting of (a) hydrogen, (b) alkyl of from 1 to 6 carbon atoms, (c) alkoxy of from 1 to 6 carbon atoms, and (d) sulfhydroalkyl of from 1 to 6 carbon atoms;

$R^3$ is one or more groups independently selected from the group consisting of (a) hydrogen, (b) halogen, (c) nitro, (d) alkyl of from 1 to 6 carbon atoms, (e) carboxyl, (f) methylenedioxy, (g) cyano, (h) halo-substituted alkyl of from 1 to 6 carbon atoms, (i) hydroxy-substituted alkyl of from 1 to 6 carbon atoms, (j) a group of the formula —$YR^4$ in which Y is O or S, and $R^4$ is hydrogen or alkyl of from 1 to 6 carbon atoms, and (k) an amine of the formula —$NR^5R^6$ where $R^5$ and $R^6$ are independently selected from hydrogen and alkyl of from 1 to 6 carbon atoms, W is selected from the group consisting of (a) hydrogen, (b) alkyl of from 1 to 6 carbon atoms, (c) amino, (d) halogen, (e) alkoxy, (f) hydroxyl, (g) alkylamino, and (h) halo-substituted alkyl;

X is selected from the group consisting of (a) hydrogen, (b) halogen, (c) alkyl of from 1 to 6 carbon atoms and, (d) halo-substituted alkyl of from 1 to 6 carbon atoms; and Z is a nitrogen-containing heterocycle of the formula

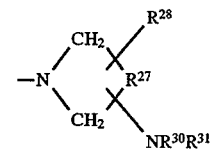

where (i) $R^{27}$ is selected from —$CH_2$—, —$CH_2$—$CH_2$—, and —$CH_2$—$CH_2$—$CH_2$—, (ii) $R^{28}$ is selected from hydrogen, halogen, alkyl of from 1 to 6 carbon atoms, halo-substituted alkyl of from 1 to 6 carbon atoms, and spirocycloalkyl of from 5 to 10 carbon atoms, and (iii) one of $R^{30}$ and $R^{31}$ is hydrogen and the other is selected from the group consisting of acetyl, α-amino acid and dipeptidyl;

or, taken together with the atoms to which they are attached, X and Z form —$OCH_2CH_2O$— or —$OCH_2O$—, with the proviso that $R^2$ is not hydrogen.

10. The compound according to claim 9 wherein Z is selected from the group consisting of norvalylaminopyrrolidinyl, alanylaminopyrrolidinyl, alanylalanylaminopyrrolidinyl, norvalylnorvalylaminopyrrolidinyl, alanylnorvalylaminopyrrolidinyl and norvalylalanylaminopyrrolidinyl.

* * * * *